United States Patent
Wong et al.

(10) Patent No.: US 10,354,745 B2
(45) Date of Patent: Jul. 16, 2019

(54) ALIGNING AND CLUSTERING SEQUENCE PATTERNS TO REVEAL CLASSIFICATORY FUNCTIONALITY OF SEQUENCES

(71) Applicant: Andrew Ka-Ching Wong, Waterloo (CA)

(72) Inventors: Andrew Ka-Ching Wong, Waterloo (CA); Annie En-Shiun Lee, Markham (CA)

(*) Notice: Subject to any disclaimer, the term of this patent is extended or adjusted under 35 U.S.C. 154(b) by 291 days.

(21) Appl. No.: 14/784,978

(22) PCT Filed: Apr. 17, 2014

(86) PCT No.: PCT/CA2014/000357
§ 371 (c)(1),
(2) Date: Oct. 16, 2015

(87) PCT Pub. No.: WO2014/169377
PCT Pub. Date: Oct. 23, 2014

(65) Prior Publication Data
US 2016/0070854 A1   Mar. 10, 2016

Related U.S. Application Data

(60) Provisional application No. 61/812,930, filed on Apr. 17, 2013.

(51) Int. Cl.
*G01N 33/48*  (2006.01)
*G01N 33/50*  (2006.01)
*G16B 30/00*  (2019.01)
*G16B 40/00*  (2019.01)

(52) U.S. Cl.
CPC ............. *G16B 30/00* (2019.02); *G16B 40/00* (2019.02)

(58) Field of Classification Search
None
See application file for complete search history.

(56) References Cited

U.S. PATENT DOCUMENTS 6,092,065 A    7/2000  Floratos et al.

OTHER PUBLICATIONS

Schreiber et al. Energetics of protein-protein interactions: Analysis of the barnase-barstar interface by single mutations and double mutant cycles. Journal of Molecular Biology, vol. 248, pp. 478-486. (Year: 1995).*

(Continued)

*Primary Examiner* — Russell S Negin
(74) *Attorney, Agent, or Firm* — Norton Rose Fulbright Canada LLP

(57) ABSTRACT

A system and method of discovering sequence patterns with variations is provided. The method includes: accessing or acquiring a data set including a family of sequences or related families of sequences; a) applying a pattern discovery process to the sequences; b) grouping and aligning the similar patterns that may have different lengths into one or more Aligned Pattern Clusters; c) discovering the co-occurrence relation between Aligned Patterns and/or Aligned Pattern Clusters to reveal the distal function between segments represented by the aligned Pattern Clusters and d) breaking down an Aligned Pattern Cluster into sub-clusters with stable cluster configuration that reveals sub-clusters with distinct and shared characteristic among sub-family of the sequences.

20 Claims, 23 Drawing Sheets

(56) References Cited

OTHER PUBLICATIONS

WIPO, International Search Report and Written Opinion for PCT Application No. PCT/CA2014/000357 dated Jul. 30, 2014.
Lee et al., Synthesizing Aligned Random Pattern Digraphs from Protein sequence Patterns, Bioinformatics and Biomedicine Workshops, 2011 IEEE International Conference on Nov. 12-15, 2011, pp. 178-185.
Lee et al., Discovering co-occurring patterns and their biological significance in protein families, From IEEE International Conference on Bioinformatics and Biomedicine, Dec. 18-21, 2013, pp. 1-13, Shanghai, China.
Lee et al., Ranking and compacting binding segments of protein families using aligned pattern clusters, From IEEE International Conference on Bioinformatics and Biomedicine, Oct. 4-7, 2012, pp. 1-14, Philadelphia, PA, USA.
Lee et al., Discovering Protein-DNA Binding Cores by Aligned Pattern Clustering, IEEE International Conference on Bioinformatics and Biomedicine, Jan. 2014, pp. 125-130, Belfast, UK.
Lee et al., Partitioning and correlating subgroup characteristics from Aligned Pattern Clusters, Bioinformatics, 2016, 32 (16), pp. 2427-2434, Oxford University Press.
Kung et al., Revealing Protein Structures by Co-Occurrence Clustering of Aligned Pattern Clusters, ACM Conference on Bioinformatics, Computational Biology, and Health Informatics, 2013, pp. 869-875, Association for Computing Machinery, Washington DC.
Lee et al., Classifying Proteins by Amino Acid Variations of Sequential Patterns, ACM Conference on Bioinformatics, Computational Biology, and Health Informatics, 2013, pp. 276-285, Association for Computing Machinery, Washington DC.
Fung, Abstract of Co-occurrence Clusters of Aligned Pattern Clusters, ACM Conference on Bioinformatics, Computational Biology, and Health Informatics, 2013, pp. 721, Association for Computing Machinery, Washington DC.
Lee et al., Comparing two Algorithms for Clustering Aligned Pattern Clusters, Middleware Doctoral Symposium, Aug. 11, 2013, Association for Computing Machinery, Chicago, IL.
Lee et al., Confirming Biological Significance of Co-occurrence Clusters of Aligned Pattern Clusters, Dec. 2013.
Sze-To et al., Prediction of Protein—Protein Interaction via co-occurring Aligned Pattern Clusters, Nov. 2016, Methods, vol. 110, pp. 26-34, Elsevier B.V.
Wong et al., Aligning and Clustering Patterns to Reveal the Protein Functionality of Sequences, IEEE/ACM Transactions on Computational Biology and Bioinformatics, May/Jun. 2014, pp. 548-560, vol. 11, No. 3.
Lee et al., Characterizing Amino Acid Variations of , Scavenger Receptors by Class Information Gain, ACM Special Interest Group on Bioinformatics, Computational Biology and Biomedical, Sep. 22-25, 2013, pp. 818-825, Washington, DC.
Sze-To et al., Predicting Protein-Protein Interaction Using Co-Occurring Aligned Pattern Clusters, IEEE in Bioinformatics and Biomedicine, 2015, pp. 55-60, Washington, DC.
Lee et al., Discovering Protein-DNA Binding Cores by Aligned Pattern Clustering, IEEE International Conference on Bioinformatics and Biomedicine, 2014, pp. 125-130.

* cited by examiner $$C^1 = \begin{pmatrix} B & E & L & L & O & W \\ M & E & L & L & O & W \\ H & E & L & L & O & * \end{pmatrix} \Big\}$$

$$C^2 = \begin{pmatrix} B & A & L & L & S \\ B & A & L & K & S \\ H & A & L & \_ & S \end{pmatrix} \Big\}$$

$$\begin{pmatrix} B & E & L & L & O & W \\ M & E & L & L & O & W \\ H & E & L & L & O & * \\ B & A & L & L & S & * \\ B & A & L & K & S & * \\ H & A & L & \_ & S & * \end{pmatrix} = C^3$$

More Amino Acid Variation in AP Sub-Clusters

Columns with high Information gain close to 1 reveal amino acid variations reflecting sub-group characteristics that might be associating with different classes.

Columns with R1 close to 1 indicates amino acid conserved in most classes

| | 71 | 72 | 73 | 74 | 75 | 76 | 77 | 78 | 79 | 80 | 81 | 82 | 83 | 84 | 85 | 86 | 87 | 88 | 89 | 90 | 91 | 92 | 93 | 94 | 95 | 96 | 97 | Mammal | Plant | Fungi | Insect | H |
|---|---|---|---|---|---|---|---|---|---|---|---|---|---|---|---|---|---|---|---|---|---|---|---|---|---|---|---|---|---|---|---|---|
| 1 | T | L | Y | D | Y | L | L | N | P | * | * | * | * | * | * | * | * | * | * | | * | * | * | * | * | * | * | 0 | 21 | 1 | 0 | 0.13 |
| 2 | * | * | * | * | * | * | * | N | P | K | K | Y | I | P | G | T | K | M | V | | * | * | * | * | * | * | * | 0 | 23 | 1 | 4 | 0.4 |
| 3 | * | * | * | * | * | * | * | N | P | K | K | Y | I | P | G | T | K | M | * | | * | * | * | * | * | * | * | 30 | 24 | 20 | 10 | 0.95 |
| 4 | * | L | F | E | Y | L | E | N | P | K | K | * | * | * | * | * | * | * | * | | * | * | * | * | * | * | * | 0 | 1 | 5 | 9 | 0.62 |
| 5 | * | L | Y | D | Y | L | L | N | P | K | K | Y | I | P | G | T | K | M | V | | * | * | * | * | * | * | * | 0 | 21 | 1 | 0 | 0.13 |
| 6 | T | L | Y | D | Y | L | L | N | P | K | K | Y | I | P | G | T | K | M | V | | F | G | L | K | K | P | Q | 0 | 18 | 1 | 0 | 0.15 |
| 7 | * | * | * | * | Y | L | L | N | P | K | K | Y | I | P | G | T | K | M | V | | F | G | L | K | K | P | * | 0 | 22 | 1 | 0 | 0.13 |
| 8 | T | L | M | E | Y | L | E | N | P | K | K | Y | I | P | G | T | K | M | | | * | * | * | * | * | * | * | 30 | 0 | 0 | 0 | 0 |
| 9 | * | * | * | E | Y | L | E | N | P | K | K | Y | I | P | G | T | K | M | | | A | G | * | * | * | * | * | 22 | 0 | 0 | 6 | 0.37 |
| 10 | T | L | M | E | Y | L | E | N | P | K | K | Y | I | P | G | T | K | M | | | A | G | I | K | K | K | * | 17 | 0 | 0 | 0 | 0 |
| | T | L | M | E | Y | L | E | N | P | K | K | Y | I | P | G | T | K | M | | | A | G | I | K | K | * | * | 20 | 0 | 0 | 0 | 0 |
| 11 | * | * | * | E | Y | L | E | N | P | K | K | Y | I | P | G | T | K | M | * | | * | * | * | * | * | * | * | 30 | 1 | 5 | 9 | 0.66 |
| 12 | * | * | * | * | Y | L | E | N | P | K | K | Y | I | P | G | T | K | M | * | | * | * | * | * | * | * | * | 30 | 1 | 16 | 10 | 0.77 |
| 13 | * | * | * | * | Y | L | E | N | P | K | K | Y | I | P | G | T | K | M | A | | G | G | L | K | K | * | * | 0 | 1 | 15 | 0 | 0.17 |
| 14 | * | * | * | * | * | * | * | N | P | K | K | Y | I | P | G | T | K | M | A | | G | G | L | K | K | * | * | 0 | 1 | 17 | 0 | 0.15 |
| IG | 0.36 | 0.18 | 0.73 | 0.47 | 0.04 | 0.04 | 0.4 | 0 | 0 | 0.01 | 0.01 | 0.01 | 0.01 | 0.01 | 0.01 | 0.01 | 0.01 | 0.01 | 0.63 | 0.03 | 0.59 | 0.03 | 0.47 | 0.14 | 0.14 | 0.44 | 0.22 | | | | | |
| R1 | 0.68 | 0.56 | 0.11 | 0.42 | 1.02 | 1.02 | 0.31 | 1.02 | 1.02 | 0.87 | 1.02 | 0.87 | 1.02 | 1.02 | 1.02 | 1.02 | 1.02 | 1.02 | 0.02 | 1.02 | 0.06 | 1.02 | 0.41 | 0.87 | 1.02 | 0.24 | 0.08 | | | | | |

- All sub-clusters are quite distinct
- Some Datterns are shared by many classes -- pattern 3 and 12

Co-occurring Patterns Discovered and Displayed in GUI

Patterns Discovered and Synthesized into Aligned Pattern Clusters
Via Normalized Entropy of Patterns
Revealing Amino Patterns of Protein Classes Statistics and
Protein Class
Characteristics

| 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 | 51 | # | Stat. Sig. | C. St. Sig | Mammal | Plant |
|---|---|---|---|---|---|---|---|---|---|---|---|---|---|---|---|---|---|---|---|---|---|---|---|---|---|---|---|---|---|---|---|---|---|---|---|---|---|---|---|---|---|
| Q | K | C | A | Q | C | H | T | V | E | K | G | G | K | H | K | - | N | P | K | K | Y | I | P | G | T | K | M | I | F | A | G | I | K | K | * | * | 20 | 3E+19 | 2E-05 | 20 | 0 |
| * | * | * | * | * | * | * | * | * | * | * | * | * | * | * | * | * | * | * | * | * | * | * | * | * | * | * | * | * | * | * | * | * | * | * | * | * | 29 | 6E+14 | 3E-07 | 29 | 0 |
| * | * | * | G | A | * | * | * | * | * | * | * | * | * | H | K | - | N | P | K | K | Y | I | P | G | T | K | M | * | * | * | * | * | * | * | * | * | 53 | 1E+08 | 1E-08 | 30 | 23 |
| * | * | * | G | A | * | * | * | * | * | * | * | G | * | H | K | - | N | P | K | K | Y | I | P | G | T | K | M | V | F | P | G | L | K | K | P | Q | 20 | 4E+14 | 3E-04 | 0 | 20 |
| * | * | * | * | * | * | * | * | * | * | * | * | * | * | * | * | * | * | * | * | * | * | * | * | * | * | * | * | * | * | * | * | * | * | * | * | * | 23 | 5E+10 | 3E-03 | 0 | 23 |
| 0.44 | 0.99 | 0.18 | 0.87 | 0.87 | 0.87 | 0.87 | 0.87 | 0.87 | 0.87 | 0.87 | 0.87 | 0.02 | 0.87 | 0 | 0 | 0 | 0 | 0 | 0 | 0 | 0 | 0 | 0 | 0 | 0 | 0 | 0 | 0.99 | 0.02 | 0.8 | 0.04 | 0.8 | 0.04 | 0.04 | 0.71 | 0.71 | | Total | | 30 | 23 |
| 0.62 | 1 | 0.83 | 0.91 | 1 | 1 | 1 | 1 | 1 | 0.7 | 0.88 | 1 | 0.77 | 0.77 | 1 | 1 | 1 | 1 | 1 | 1 | 1 | 1 | 1 | 1 | 1 | 1 | 1 | 1 | 0.77 | 1 | 0.66 | 1 | 0.74 | 1 | 1 | 0.7 | 0.46 | | | | | |

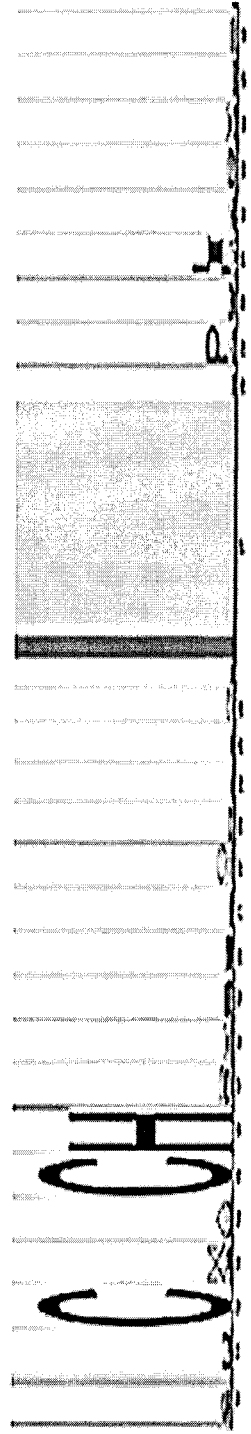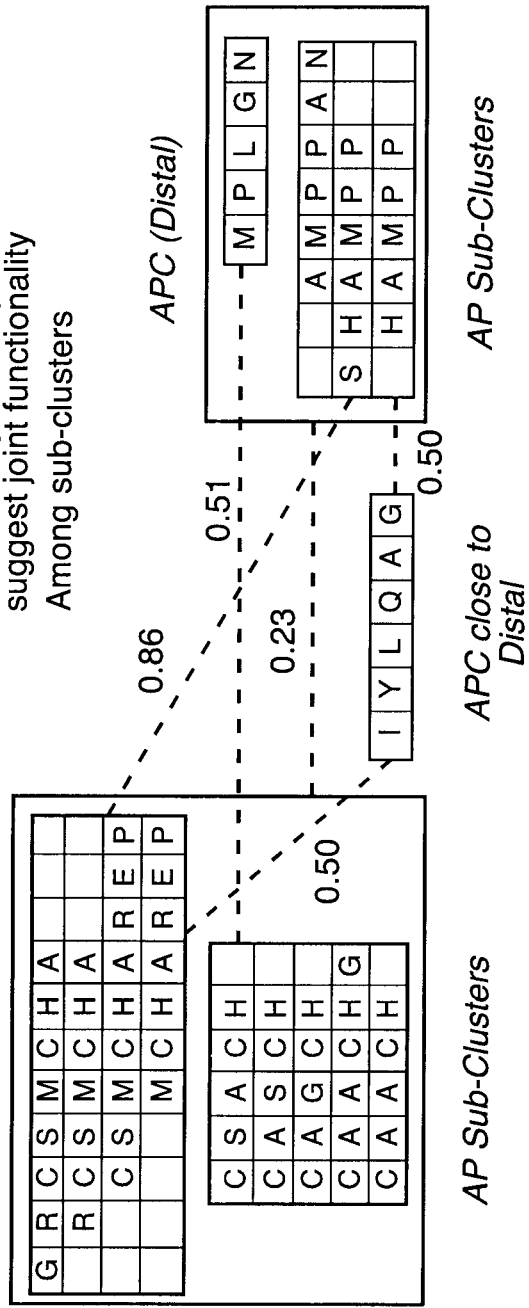
FIG.19

ALIGNING AND CLUSTERING SEQUENCE PATTERNS TO REVEAL CLASSIFICATORY FUNCTIONALITY OF SEQUENCES

CROSS-REFERENCE

This application claims the benefit of U.S. Provisional Patent Application No. 61/812,930 filed Apr. 17, 2013, which is hereby incorporated by reference in its entirety.

FIELD OF THE INVENTION

This invention relates generally to pattern detection on sequences, including biosequences. This invention further relates to analysis and discovery of macromolecular patterns.

BACKGROUND OF THE INVENTION

In macromolecular analysis (such as proteins, DNA, or RNA), discovering sequence patterns with variations may reveal the underlying function of a protein family. Protein motifs or patterns (including RNA/DNA patterns) are conserved regions with variations that are maintained in the amino acid or residues respectively, whether the significance of these motifs be structural, functional, or evolutionary.

Macromolecular analysis may be directed for example at detecting sequence patterns that may reveal the underlying function of a protein family. Discovering these sequence patterns with variations is used for example in drug discovery.

Functional patterns can be altered through mutation, and therefore they do not repeat precisely at the same location for each occurrence of the protein, which poses a challenge in discovering and analyzing these patterns.

Various prior art bioinformatics techniques may be used for functional pattern discovery. These are generally based on one of two approaches: (1) multiple sequence alignment, or (2) motif finding.

Multiple sequence alignment can align a set of protein sequences from the same protein family in order to identify important regions and sites in the resulting alignment. Common multiple sequence alignments include Clustal Omega, T-Coffee, DIALIGN, and HMMER. However, finding the global optimal alignment is expensive to compute, and is known to be an NP-complete problem in regards to its computational complexity. Even with approximate heuristics added, multiple sequence alignment is not efficient in handling large datasets. Moreover, this approach is only appropriate for highly similar sequences, but not for sequences with considerable dissimilarity. Therefore, instead of aligning the entire sequence globally, it is only suitable to identify similarities locally. Thus, the suspected consensus regions may need to be located and pre-processed ahead of time.

Motif finding generally involves using combinatorial and probabilistic methods to identify protein function segments. Furthermore, these prior art solutions are generally based on finding patterns. For example, many combinatorial methods exhaustively enumerate all possible sequence patterns and derive the best consensus pattern taken from the enumerated results. One prior solution is known to create cliques in which vertices are sequence patterns while arcs connect similar sequence patterns. The cliques then represent the consensus patterns.

Furthermore, prior art probabilistic methods generally calculate the amino acid distribution at each fixed position to form an array of sequence patterns. One example involves a position-specific weighted matrix, which estimates an amino acid at each position while assuming that each position is independent. An alternative method, known as the random sequence synthesis, takes frame-shifted position into consideration by optimally aligning amino acids to create a probabilistic sequence representation known as random sequences. Other probabilistic methods make use of a Markov model, where the dependencies of the current state depend only on a pre-specified set of past states. This is the case for example with the popular pFAM™ database (referred to below), which builds a profile Hidden Markov Model (HMM) from the multiple sequence alignment of a protein family for classifying proteins and predicting their functionality. In general, the probabilistic models compress the data into probability distributions and express amino acid associations as a sequence of independent random variables. With such a method, although each position has its amino acid distribution, there is no specific way to express the complex amino acid associations with statistical support within the sequence patterns.

Examples of known protein annotation databases include pFAM (already mentioned) or PROSITE™. Also, various computer system and computer programs are known that incorporate motif finding feature or functions for example: CONSENSUS™, MEME™, Gibbs™ or BLOCKS™.

A common problem is that these technologies and methods generate large solutions sets. In part to manage these large solution sets, prior art technologies are constrained to, or are usually used so as to, limit analysis to the same or similar macromolecule families.

Furthermore, probabilistic motif finding requires a more elaborate representation of amino acid associations, which is not available in prior art solutions.

What is needed is a computer system and method that addresses some of these limitations.

SUMMARY OF THE INVENTION

In one aspect, a method of discovering sequence patterns with variations is provided comprising: (A) accessing or acquiring a data set including a family of macromolecular sequences ("sequences"); (B) applying a pattern discovery process to the sequences so as to generate sequence patterns based on the statistical significance association of their residues; and (C) grouping and aligning the similar patterns that may have different lengths into one or more Aligned Pattern Clusters. The method enables (A) the verification of results base on their class labels, (B) the identification of multiple sequences that are closely or not closely related or are in substantially distal regions, and (C) the analysis of relationships among these clusters.

A skilled reader will understand that the functions or processes described may be implemented in a number of ways for example using a computer implemented method or computer system. The computer implemented method or computer system may include for example a computational process or algorithm for implementing the functions or features described.

In a further aspect, the pattern discovery technique generates non-redundant, statistically significant patterns which have associations within, between and among the sequences.

In a still further another aspect, the pattern discovery process discovers and obtain a reduced list of non-redundant statistically significant association patterns; in addition, the Aligned Pattern Clusters further reduce the list by grouping and aligning similar patterns. The various amino acid associations of all patterns in the Aligned Pattern Clusters are retained so as to capture the variations as well as the similar patterns there between.

In another aspect, a further step includes applying one or more statistical analysis methods to either support the analysis of the Aligned Pattern Clusters or the amino acids distribution on their columns.

In yet another aspect, a further step includes using the Aligned Pattern Clusters (AP Clusters) to generate a knowledge-rich representation of the sequence patterns as Aligned Pattern Digraphs, Class Profiles, Co-Occurrence AP Clusters, Relational Cluster Pairs, Stable Sub-Cluster Configuration within AP Clusters, AP Cluster Relational Graphs and AP Cluster Co-Occurrence Graph (AP Cluster C-Graph).

In another aspect, a bioinformatics system is provided comprising: (A) one or more computers; the one or more computer being linked to a sequence pattern discovering utility, which when executed: (i) applies to a data set including a family of macromolecular sequences ("sequences") a pattern discovery computational process so as to generate sequence patterns based on the statistical significance association of their residues; and (ii) groups and aligns the similar patterns that may have different lengths into one or more Aligned Pattern Clusters that enable the analysis of multiple sequences that are closely or not closely related or are in substantially distal regions.

In another aspect of the bioinformatics system, one or more of the computers is linked to a display and the sequence pattern discovering utility includes or is linked to a visualization tool that uses the Aligned Pattern Clusters to generate a knowledge-rich representation of the sequence patterns.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

BRIEF DESCRIPTION OF THE DRAWINGS

In the drawings, embodiments of the invention are illustrated by way of example. It is to be expressly understood that the description and drawings are only for the purpose of illustration and as an aid to understanding, and are not intended as a definition of the limits of the invention.

FIG. 2 illustrates, in a representative example, the generation of an AP cluster, and iterative steps involved in the hierarchical clustering of aligned patterns into an AP Cluster or an AP Digraph.

FIGS. 5 and 6 illustrates alternative protein structure visualizations that are based on the results of pattern discovery and the aligned pattern clustering in accordance with the present invention.

FIG. 10 further illustrates the AP clusters and the classification, as well as the measures, such as class entropy (H), class information gain (IG), and redundancy measure (R1).

Figure 12:
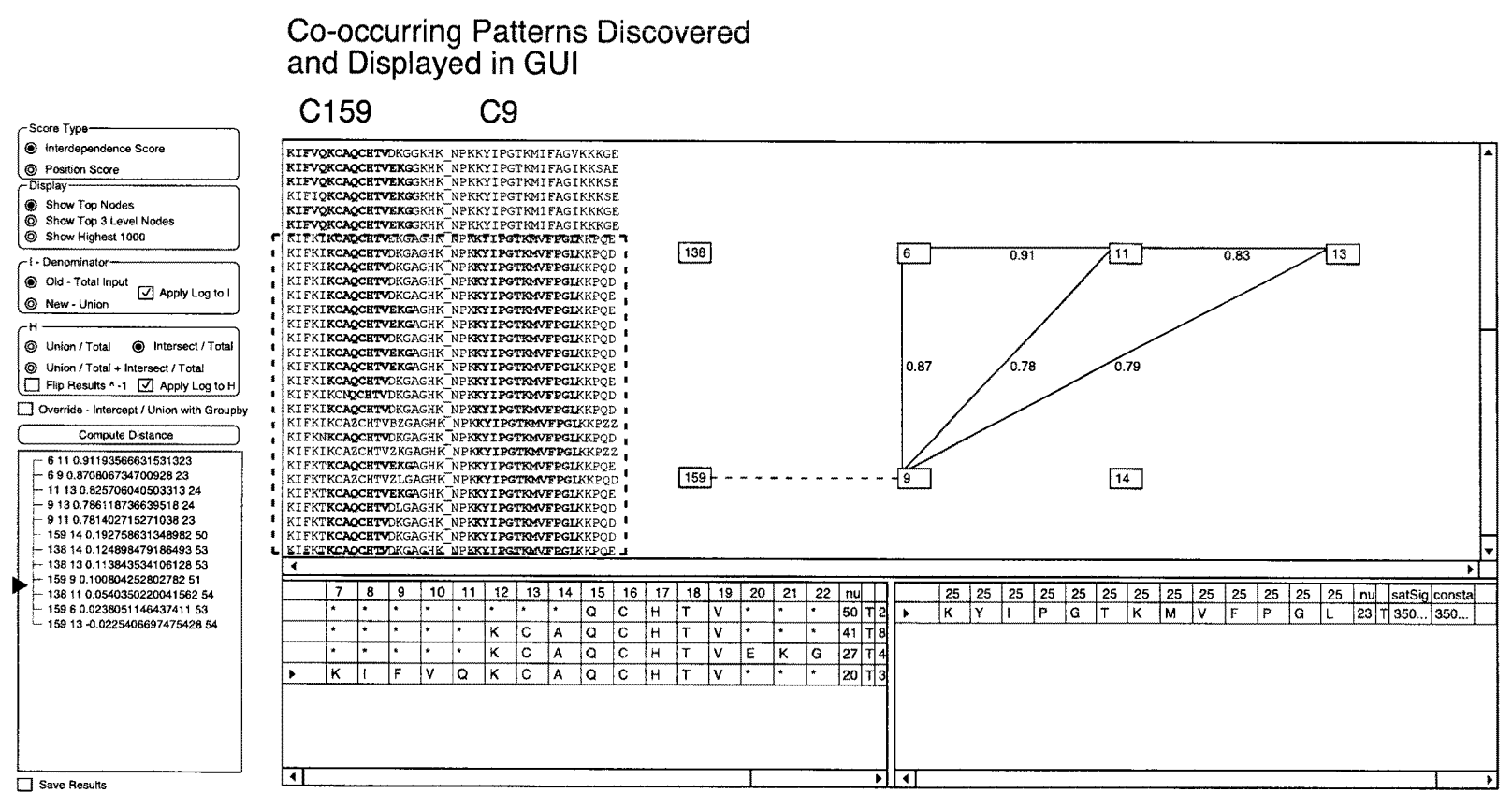

FIG. 12 illustrates a possible GUI for discovering patterns, generating aligned pattern clusters, finding aligned pattern cluster relationships (co-occurrence) and relational graph, in a particular view that provides an overview of the use of the GUI shown to generate statistics and protein class characteristics.

Figure 13:
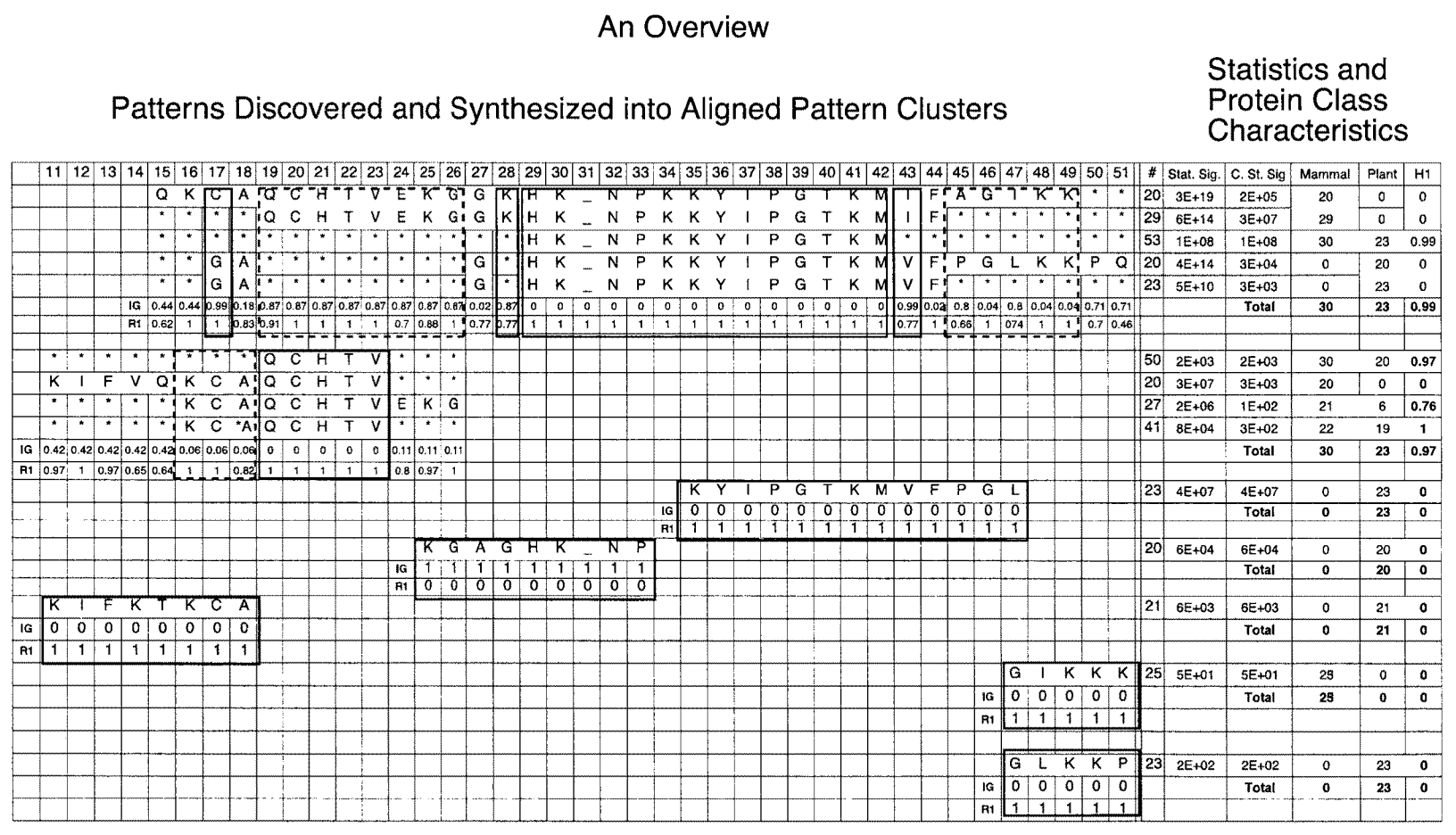

FIG. 13 shows a further possible view of the GUI of FIG. 12 for revealing classification of characteristics, particularly for AP Clusters that span multiple classes and AP Clusters that belongs to only one class.

FIG. 14 shows a further possible GUI for discovering patterns and generating aligned pattern clusters for classification, specifically measure of class entropy across patterns.

Figure 15:
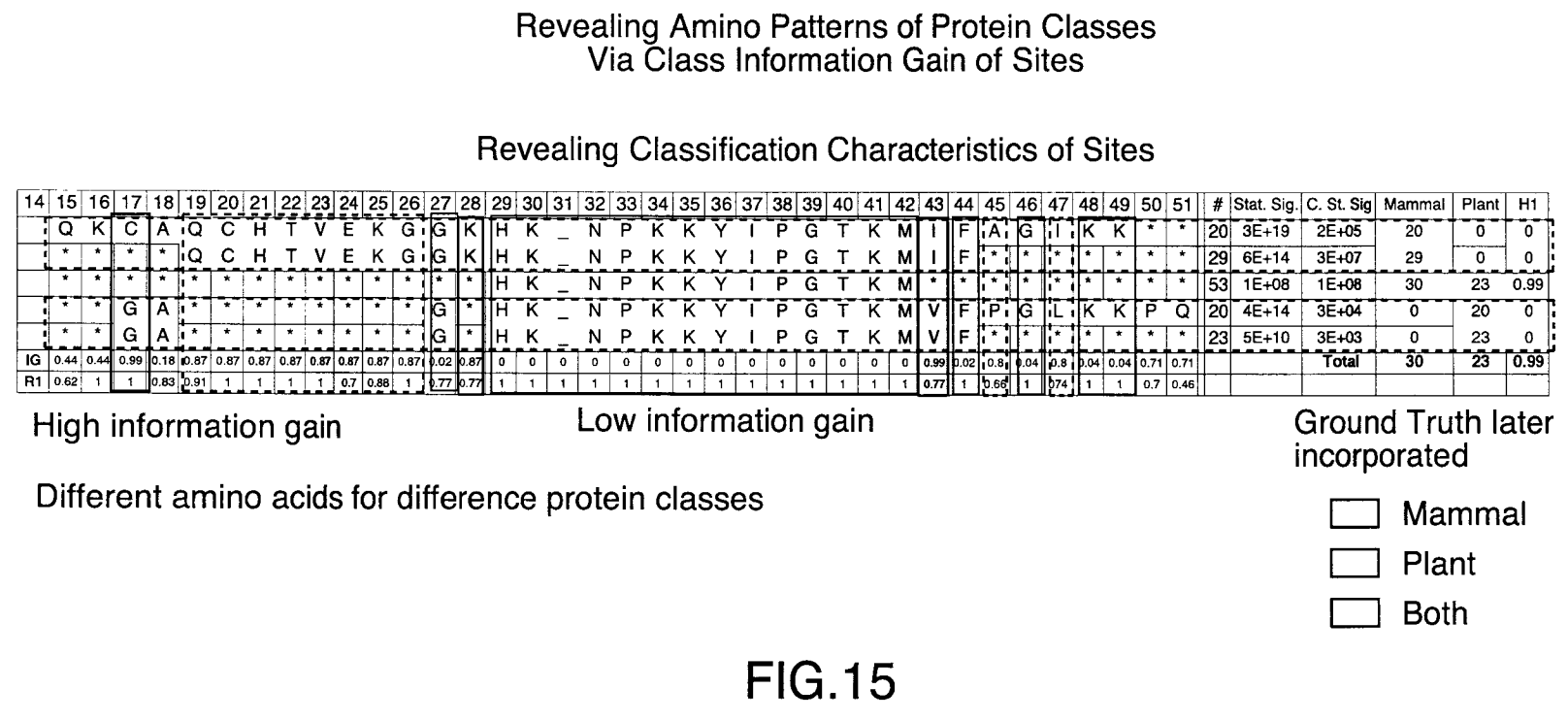

FIG. 15 shows a further possible view of the GUI of FIG. 10 for revealing classification characteristics of sites (aligned columns).

FIG. 19 further illustrates dusters of co-occurring APCs which suggest joint functionalities, in accordance with another aspect of the invention.

DETAILED DESCRIPTION

Figure 1A:
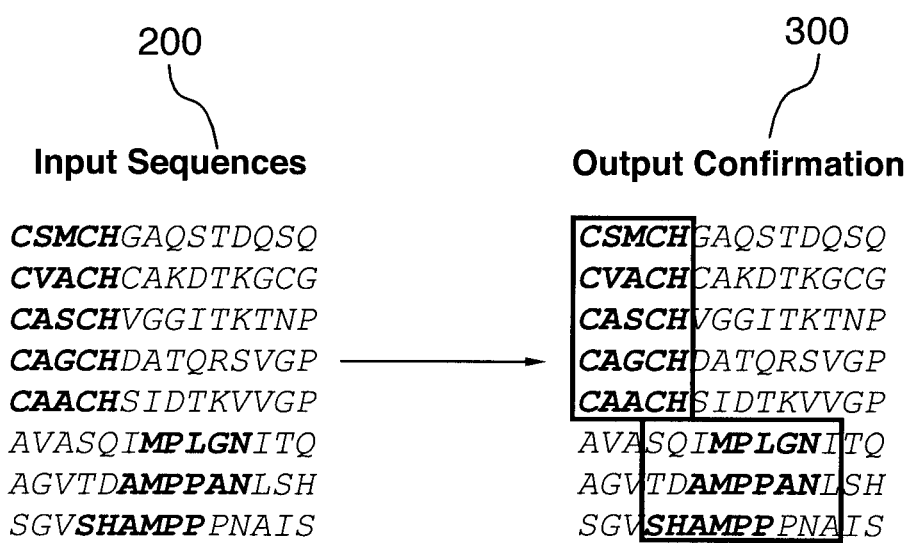
FIG. 1a illustrates a) input sequences 200 and the parts of these that contain patterns, in connection with an example of the cytochrome c protein, that represent binding sites and b) the output patterns 300 discovered from the input sequences which, are aligned and clustered into two Aligned Pattern Clusters based on the similarity measure and the optimal pattern alignment therein.

The present invention provides a technique to obtain amino acid associations in a new and innovative way, that is much more efficient than what is possible using prior art techniques, by discovering sequence patterns, clustering and aligning them for the first time into Aligned Pattern Clusters ("AP Clusters") using a new AP Clustering and Synthesis Process. As disclosed below, a technique has been developed in this invention for discovering, aligning and synthesizing AP Clusters from input sequences of a protein or RNA or DNA family using a new and innovative AP Synthesis Process.

In another aspect of the invention, the amino acid or residue association generation technique described enables the display of these associations for the first time in a knowledge-rich representation of sequence patterns and aligned pattern clusters and their co-occurring and other relations within and between related sequences. More particularly, analysis data generated by the present invention may be integrated with a variety of known data visualization techniques to provide more effective decision support to researchers. Also, the present disclosure includes data representations that are novel and innovative per se.

In a still further aspect of the invention, the amino acid association generation technique of the present invention may for the first time be integrated with statistical support, if required, in order to generate further variations and permit analysis of associations produced by the technique.

Significantly, these sequence patterns are generated in a way that much more computationally efficient than is possible using prior art techniques. This is accomplished in part because the use of statistically significant sequence patterns discovered ahead in the AP clustering compact the solutions generated by sequence pattern discovery, by revealing a reduced set of candidate solutions without losing information.

Rather than being based on residue alignment, the computer system and method of the present invention is pattern based. Pattern discovery, in accordance with the novel and innovative approach disclosed herein, is applied to a set of macromolecular sequences, to discover, locate, cluster and align patterns in an integrated process and therefore as explained below the present invention reveals localized (within for example a sequence) functionality or features (A) in a more concise manner (that is easier to understand and use for example in connection with analytical or discovery efforts), and also (B) in a way that reveals associations between/among the revealed patterns such as taxonomical variation therein, as well as other family characteristics.

Furthermore, because the present invention is pattern based this means that the output from the computer system and computer implemented method is generated quickly and in a stable manner.

The technique described can be applicable not only to biosequences but more also more broadly to other types of sequences. Also, the present invention may be applied to other data sets with similar properties in the sense that the data sets may be aligned and clustered in order to discover patterns between sub-sets. Other application of the invention include sequence patterns that contain continuous values and multiple sequences that contain discrete and/or continuous values. Preprocessing for Continuous Sequence requires discretizing the continuous numbers to discrete intervals before feeding. Preprocessing for Multiple Sequence requires slicing the multiple sequences vertically and arranging into a single sequence before processing.

Disclosed herein is a novel and innovative adaptation of AP Clustering, which may be referred to herein as a "Aligned Pattern (AP) Clustering and Digraph Synthesis" that permits the identification and visualization of for example amino acid (or RNA/DNA) protein associations, DNA or RNA family functional segments (such as binding segments) as well as functional residues in such segments (such as binding residues). In this disclosure all of such information may be referred to as macromolecular information.

The technology of the present invention is based in part on a sequence pattern discovery technology for discovering and pruning redundant sequence patterns in multiple sequences, which has been implemented as a fast algorithm that discovers functional units in sequences without relying on prior knowledge of the subject matter being analyzed/visualized. The pattern discovery technology was applied for example to time sequence analysis in order to provide a solution for pattern-based intelligent control and monitoring, as described in A. K. C. Wong and G. C. L. Li, "System, Method and Computer Program for Pattern-Based Intelligent Control and Monitoring", U.S. patent application Ser. No. 13/141,944.

The pattern discovery technique described can be adapted to discover patterns in macromolecular information, as a mechanism to improve upon sequence pattern discovery. The technology described herein enables improved analysis of patterns in macromolecular information by aligning and clustering a large number of sequence patterns discovered from families of multiple sequences into at least one Aligned Pattern (AP) Cluster and Digraph.

Significantly, the Aligned Pattern (AP) Cluster and Digraph reveals associated functional regions both within close-by regions and also substantially distal regions, including across multiple sequences and/or families (protein-protein, protein-RNA, RNA-RNA). Also, a synthesized Aligned Pattern (AP) Cluster and Digraph as disclosed herein can reveal a visualized macromolecular composition in a compact and efficient way.

A skilled reader will understand that prior art solutions generally enable the analysis and alignment of only similar macromolecular sequences, or on close-by regions. The analysis of multiple sequences that are not closely related or of substantially distal regions, using prior art solutions, generally involves by necessity significant manual work. Therefore, one of the advantages of the present invention is to automate or render more efficiently these manual processes, thereby reducing the effort and cost involved in wet biology laboratories, epidemic infective disease control and drug discovery for example.

The improved results provided by the present invention are in part because the pattern discovery based technique describe herein does not require knowledge of the relationships between the constituent elements, and therefore enables the analysis of substantially distal regions or across multiple sequences and families using a computer system and in a computationally efficient way. Also, as a result, the present invention provides a far more robust discovery tool for use in a variety of applications (as further explained below).

In another aspect, the present invention enables the representation of patterns with variation in order to reveal macromolecular associations that may be located in (i) proximal, (ii) interlacing, and (iii) distal functional segments/regions. The computer system and computer implemented method of the present invention reveals binding regions as well as the hierarchical variation of discovered AP Clusters.

As described elsewhere in this disclosure, Aligned Pattern Cluster (AP Cluster) based approach can be applied to reveal the structure and function of RNA/DNA/Protein molecules.

Moreover, the application of AP Cluster can reveal binding segments in proteins, secondary structures and tertiary structure/interactions in tRNA, as well as ribosomal RNA and long distance relationships of AP Clusters in various bio molecular sequences. A significant challenge in adapting AP Cluster to the described use is to execute the pattern discovery in a way that enables polynomial execution rather than exponential runtime complexity and automatically map the location of these discovered patterns. To this end, in accordance with one particular aspect of the present invention: the computer system and method of the present invention (1) discovers a shorter list of non-redundant statistically significant association patterns in a first step, and (2) aligns and clusters similar sequence patterns wherever they are located in the next step in order to address the probabilistic issue, retains the amino acid association of all the patterns in the aligned pattern cluster, capturing their variations as well as their similarities. These amino acid (RNA/DNA) associations retained by the AP Clusters and and/or associations of AP Clusters can reduce the number of amino acids (RNA/DNA) associations of interest, thus averting time-consuming simulations and experimentations.

Furthermore, after securing AP Clusters created from statistically significant patterns, the pattern discovery investigation can be expanded to include similar patterns in other sequence segments using a suitable subsequence alignment algorithm to expand AP Cluster to include patterns below the statistic threshold in step one, this is the AP Cluster Refinement/Extension operation. This point illustrates the flexible and user driven search strategies that can be conducted in a robust way, which are not possible, or at least not computationally efficient, using prior art technologies.

The AP Cluster Refinement/Extension operation enables improvement of the sequence coverage while attempting to maintain the low entropy of the AP clusters. In one aspect, the present invention can generate two sets of refined/extended AP Clusters, namely the Weak AP Clusters and the Conserved AP Clusters. Higher mutational variation allows more sequences to be covered by the Weak AP Cluster. In another aspect, Weak AP Clusters may be further refined to the Conserved AP Clusters by restricting the Conserved Columns, and thus decreasing the entropy.

Further Details Regarding Aligned Pattern (AP) Synthesis

In one aspect of the invention, the AP Synthesis Process includes: (1) a novel and innovative pattern discovery technique, and (2) an AP Clustering technique. (1) The pattern discovery technique discovers the most important sequence patterns amongst a family of sequences, producing non-redundant, statistically significant associations of amino acids (DNA/RNA and other residues/sites). (2) The AP Clustering technique groups and aligns these discovered patterns into AP Clusters, even though the occurrences of the pattern start at different positions in their input sequences.

Optionally, an additional technique may be provided for measuring and ranking results from the pattern discovery and AP Clustering, as explained below.

(1) Pattern Discovery

The equation below illustrates the problem of sequence patterns with variations, $\Sigma$ represents the set of elements $$\Sigma=\{\sigma_1,\sigma_2,\ldots,\sigma_{|\Sigma|-1},\sigma_{|\Sigma|}\}$$

A set of multiple sequences can be illustrated by:

$$S=\{s^k|k=1,\ldots,|S|\}=\{s^1,s^2,\ldots,s^{|S|-1},s^{|S|}\}$$

The Pattern Discovery step may be illustrated by providing a set of unaligned pattern elements:

$$\bar{P}=\{\bar{p}^i|i=1,\ldots,|\bar{P}|\}=\{\bar{p}^1,\bar{p}^2,\ldots,\bar{p}^{|\bar{P}|-1},\bar{p}^{|\bar{P}|}\}$$

where a set of unaligned patterns is one that corresponds to a resulting set of aligned pattern P, namely:

$$P=\{p^i|i=1,\ldots,|P|\}=\{p^1,p^2,\ldots,p^{|P|-1},p^{|P|}\}$$

The aligned pattern is of a fixed length as defined by Aligned Pattern Cluster Cl, which is further explained below.

FIG. 1a illustrates a possible implementation of pattern discovery as the first step of the present invention, showing parts of the cytochrome c protein that represent the binding sites thereof, where a pattern discovery technique is applied to the "input sequences" and then using the AP clustering technique to obtain AP Clusters as displayed as part of the "output confirmation".

Figure 1B:
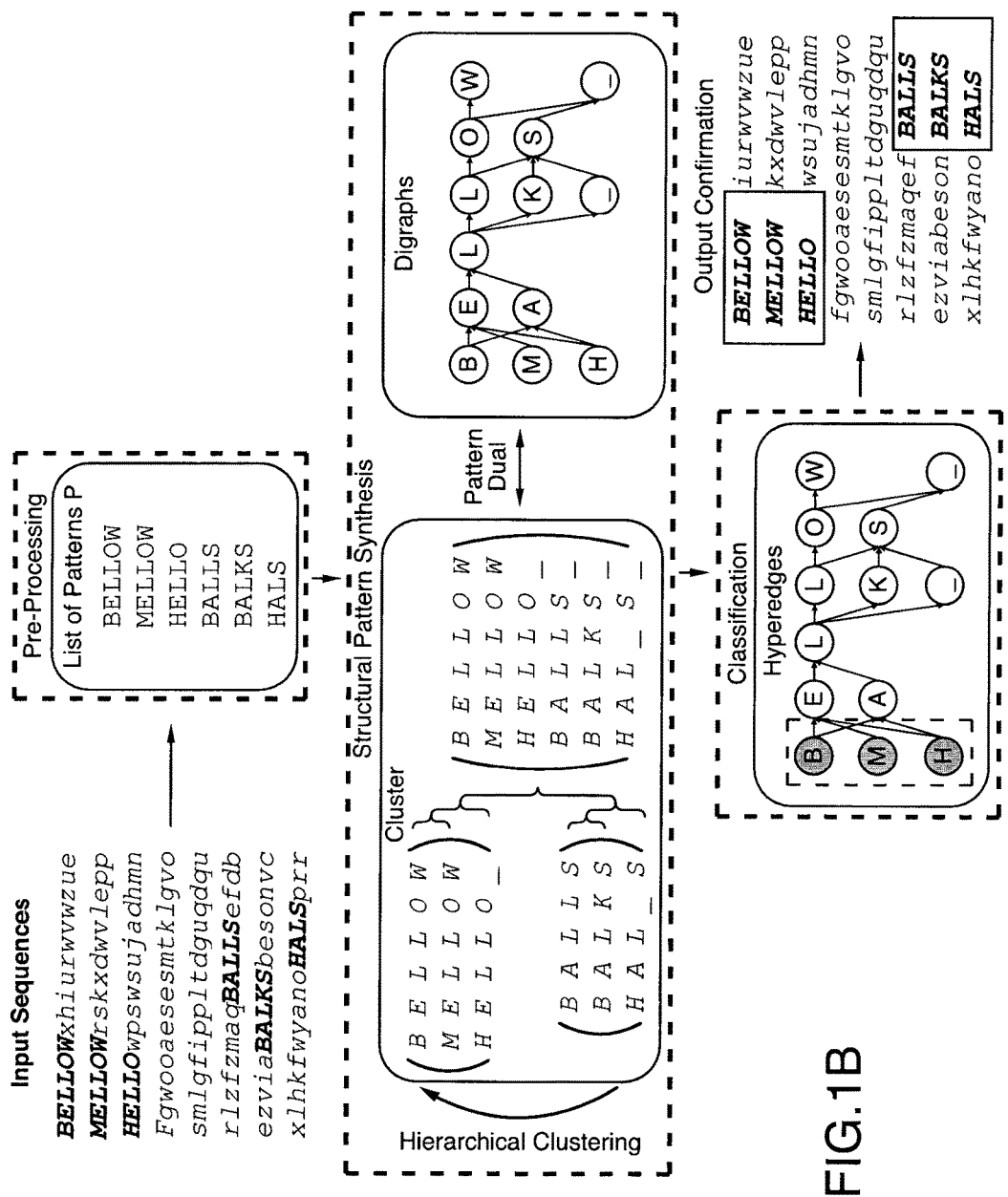
FIG. 1b illustrates an exemplary process of determining output patterns based on input sequences.

Similarly, FIG. 1b illustrates an exemplary process of determining output patterns based on input sequences.

The text example (Table 1) displays three patterns corresponding to our definition. The dataset contains three functional patterns of English words, HELLO, MELLOW, and BELLOW, which are embedded in fifteen multiple sequences S={s1, ..., s15}. The letters outside the patterns are stochastically generated from 26 characters in the English alphabet that are identically and independently distributed.

TABLE 1

| Example of Patterns $p^{-1}$ = HELLO, $p^{-2}$ = MELLOW, and $p^{-3}$ = BELLOW | | |
|---|---|---|
| S | The Input Sequences | Class |
| $s^1$ | bdxejrtewkwkHELLOkcmstsjavtpi | happy |
| $s^2$ | nfixtHELLOuzdovcaaxnkjifjcvwk | happy |
| $s^3$ | dimtndvkjmkHELLObkcmstsj | happy |
| $s^4$ | tzhgarzofdHELLOpwkxmc | happy |
| $s^5$ | tyjxjqnyHELLOwmopemlqfgptnwnq | happy |
| $s^6$ | kntywtoaxMELLOWbtlasycma | happy |
| $s^7$ | jilxchitivMELLOWriiiweyfzgvuyaa | sad |
| $s^8$ | hmlzvMELLOWorgfeb | sad |
| $s^9$ | xhmlzvqgcanyMELLOWgbfj | sad |
| $s^{10}$ | vqgcanyffcMELLOWvcnsnjvalbdvr | sad |
| $s^{11}$ | cbpyhejgkinrphceBELLOWndwzahvkitagtt | sad |
| $s^{12}$ | ndwlofBELLOWscktbucwqnboeaaklknsrmur | sad |
| $s^{13}$ | fzomphnlrqhupkqBELLOWyutpfu | angry |
| $s^{14}$ | skwybrfiBELLOWyvvxjdijwqjvs | angry |
| $s^{15}$ | nknhqexqieaBELLOWybnvrhpnsjnfms | angry |

The pattern discovery step yields a set of similar patterns of different lengths.

A skilled reader will understand that various different pattern discovery techniques may be used, provided that they yield a set of similar patterns that may be of different lengths.

(2) Aligned Pattern Clustering (AP Clustering or APC)

In the AP Clustering step, in one aspect of the invention, the set of similar patterns of different lengths obtained from the Pattern Discovery Step can be grouped and, at the same time, aligned into a set of patterns of the same length by inserting gaps and wildcards. These patterns are aligned into a cluster where the corresponding amino acids amongst the patterns are aligned into aligned column(s), thus reflecting functionality of the sequence in each row of the patterns as well as implying a common functionality among the aligned columns of the patterns.

The AP Clustering Step may be implemented using for example a single-linkage hierarchical clustering technique (which may be implemented using another suitable clustering algorithm) that takes an input of a list of patterns and then synthesizes, or more precisely, aligns and groups, them into one or more AP Cluster(s). The AP Clustering steps may be further illustrated with an additional example. This may be understood by referring to FIG. 2, in which one iteration of the hierarchical clustering algorithm is illustrated. More precisely, it shows the last step of the iterative merge between AP Cluster C1 and AP Cluster C2, thereby creating the new AP Cluster C3. FIG. 2 continues with the example of the words HELLO and MELLOW to illustrate this concept. More specifically in FIG. 2, an existing AP Cluster, C1 with m=3 and n=6, is merged with another AP Cluster, C2 with m=3 and n=5, to result in the new AP Cluster, C3, which is extended to m=6 and n=6.

A set of AP Clusters are optimally grouped and vertically aligned into a set of patterns represented by $C^l$ or Cl, as follows:

$$C^l = \text{ALLIGN}(P^l)$$

$$C^l = \begin{pmatrix} s_1^1 & s_2^1 & \ldots & s_n^1 \\ s_1^2 & s_2^2 & \ldots & s_n^2 \\ \vdots & \vdots & \vdots & \vdots \\ s_1^m & s_2^m & \ldots & s_n^m \end{pmatrix}_{m=n} = \begin{pmatrix} p^1 \\ p^2 \\ \vdots \\ p^m \end{pmatrix}$$

$$C^l = (c_1 \ c_2 \ \ldots \ c_n)$$

Let $\Sigma(c_j)$ be the set of distinct amino acids in an aligned column $c_j$ such that $\Sigma(c_j) = \{s_j^i = \sigma | p^i = s_1^i \ldots s_j^i \ldots s_n^i, p^i \in p^i, \sigma \in \Sigma \cup \{-\} \cup \{*\}\}$. Further denote $\sigma(c_j)$ as an amino acid in $\Sigma(c_j)$.

In a further aspect of the invention, induced data D(Cl) is generated, consisting of the data induced by Cl or in other words the induced data of Cl. D(Cl) is the union of the segments from input sequences induced by all of the patterns of (Cl) that is:

$$\mathbb{D}(C^l) = \mathbb{D}(p^1) \cup \mathbb{D}(p^2) \cup \ldots \cup \mathbb{D}(p^m) = \bigcup_{\forall p^i \in P^l} \mathbb{D}(p^i)$$

In one aspect, the synthesis of the AP Clusters enables the representation of for example protein functional patterns that capture both statistically significant associations of the amino acids in the sequence pattern as well as their variations and similarities on each of the aligned columns. More precisely, the present invention aligns and groups similar sequence patterns with variations to form a cluster of Aligned Patterns and to examine whether or not the AP Clusters correspond to the binding segment and its aligned columns correspond to binding residues that reflect the protein's functionality.

Measuring and Ranking Results of AP Cluster

In another aspect of the present invention, AP Clusters generated are measured and ranked.

Ranking may be accomplished by (A) measuring the statistical significance and/or tightness of AP Clusters using one or more suitable measuring mechanisms, and (B) ranking the measured AP Clusters, using one or more ranking methods.

One of the many advantages of the present invention is that the AP Clusters may be used as input to one or more statistical methods. In other words, the generation of the AP clusters enables implementation through the computer system of the present invention of statistical support to increase the effectiveness of discovery, clustering and alignment of patterns as well as techniques to enhance its ranking and revelation precision of the inherent functional characteristics based on the present invention.

For example, in one specific implementation of the present invention, one or more measurement mechanisms may be applied to each AP Cluster, for example to support ranking of AP Clusters. These measurement mechanisms may include: (a) Coverage, (b) AP Cluster Quality, and (c) Standard Residual measure.

A skilled reader will appreciate that various measurement mechanisms may be applied.

"Coverage" accounts for the total input sequences covered by a given AP Cluster, over the entire set of input sequences. Coverage consists of counting the number of occurrence in the induced data space D(Cl).

"AP Cluster Quality" is the average column entropy subtracted from one, where entropy is computed from the set of Aligned Patterns. AP Cluster Quality measures the stability or reliability of an AP Cluster, whereas entropy measures the randomness or variation within an AP Cluster. Where AP Cluster Quality approaches a value of "one", the resulting AP Cluster is more stable. Where AP Cluster Quality approaches "zero", the AP Cluster is more random.

"Standard Residual" measures the statistical significance of the AP Cluster by comparing the actual number of occurrences of all of the patterns included in a particular AP Cluster, against the expected number of occurrences, which is computed from a default random model of the AP Cluster. In one aspect, an assumption is made that each of the aligned columns of an AP Cluster are independent and identically distributed. A sum of probability of all possible amino acids being in one single aligned column is used to compute a default probability of an aligned column in a given AP Cluster.

Additionally, (1) a redundancy measure and (2) an average sum of redundancy may be applied to aligned columns. (1) The redundancy measure indicates the specificity or stability of the amino acids in an aligned column based on the frequency of the occurrences of the amino acids taken from that aligned column. (2) The average sum of redundancy indicates the stability of an aligned column with respect to another aligned column. These information theoretic measures are especially effective and revealing when applied to Weak AP Clusters, their induced data, and conditional probabilities restricted on the pattern.

Aligned Pattern Digraph—for Representation and Computation

An Aligned Pattern Digraph (AP Digraph) considers each unique amino acid as a vertex for the purposes of easy visualization and computation. The compact representation shows the flow of patterns from one amino acid position to the next in a linear (binary edge) relationship.

Figure 16A:
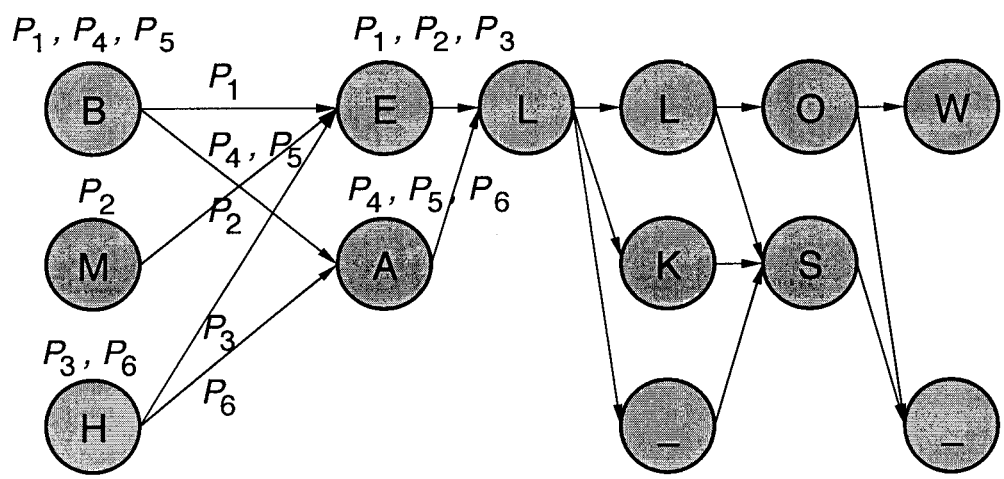
FIG. 16a shows an exemplary AP Digraph.
Figure 16B:
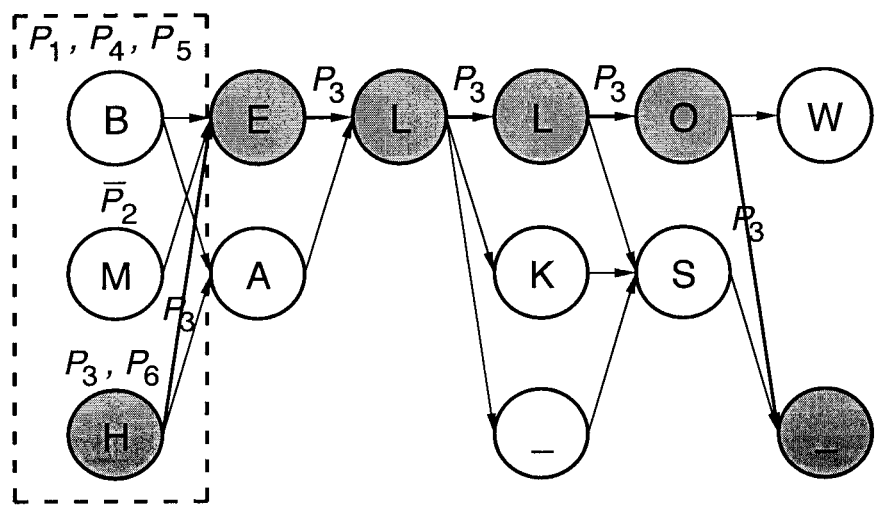
FIG. 16b shows an exemplary diagraph of an aligned column hyperedge.

As shown in FIG. 16a, an AP Digraph is a directed graph, G=($\mathbb{V}$, $\mathbb{E}$), where vertices and directed edges are defined as follows:

$\mathbb{V} = \{v_j(\sigma) | 1 \leq j \leq n, \sigma \in \Sigma, \mathbb{P}(v_j(\sigma)) \neq \emptyset\}$, where $\mathbb{P}(v_j(\sigma)) = \{P \in \mathbb{P} | s_j^i = \sigma\}$ $\mathbb{E} = \{\in_j(v_j(\sigma), v_{j+1}(\sigma')) | 1 \leq j \leq n, \sigma, \sigma' \in \Sigma, \mathbb{P}(v_j(\sigma)) \cap \mathbb{P}(v_{j+1}(\sigma')) \neq \emptyset\}$ As shown in FIG. 16b, an aligned column hyperedge is the jth aligned column such that, $W^j = \{\mathbb{P}(v_j(\sigma)) | \sigma \in \Sigma, \mathbb{P}(v_j(\sigma)) \neq \emptyset\}$.

Breaking Down AP Clusters into a Stable Sub-Cluster Configurations

As the functionality of protein segments associated with the discovered AP Clusters is confirmed by the classification described elsewhere in this disclosure, a new method can be introduced that autonomously breaks down the AP Clusters into sub-clusters with an optimal and stable sub-cluster configuration to reveal the inherent taxonomical/class characteristics of the protein segments contained in the AP Cluster without relying on prior knowledge. The purpose of this step is to further separate the patterns into sub-clusters autonomously so as to reveal pattern subgroups some of which may associate with more distinct sub-family characteristics (like taxonomical grouping) and some may be shared by most segments associated with the patterns in the AP Cluster. Such partition of patterns cannot be obtained when AP Clusters are clustered based just on similarity. To this end, a more objective sub-cluster separability measure is introduced to optimize the separation and distinction of the sub-clusters. Hence, a separability measure may be provided that minimizes the average normalized attraction between sub-clusters obtained from an AP Cluster is based on an inverse distance square rule between sub-clusters, a concept borrowed from electrostatic repulsion among objects with the same charge. Also, there are outlying patterns that are clustered weakly or incorrectly that can be discovered by the optimal cluster configuration.

A skilled reader will understand that other measures may be used instead of separability measures, such as edge weight, average edge weight, or AP Cluster density.

To break down the AP Cluster, a graph theoretical clustering approach can be used. The AP Cluster is represented as a completed weighted graph where each vertex represents a pattern and/or and the weight of each edge is the distance between the patterns and/or normalized average distances between AP Clusters represented by its incident vertices.

To obtain sub-clusters, a minimum (in this case, a maximum as repulsion is used as distance) weighted spanning tree is first obtained from the complete graph. Sub-clusters are obtained by cutting the edge of the spanning tree. To obtain an optimal sub-cluster configuration, a separability measure as mentioned in the previous section is used. For a set of patterns, the sub-cluster configuration of them is the most stable or optimal one if its separability measure is maximized.

Figure 11A:
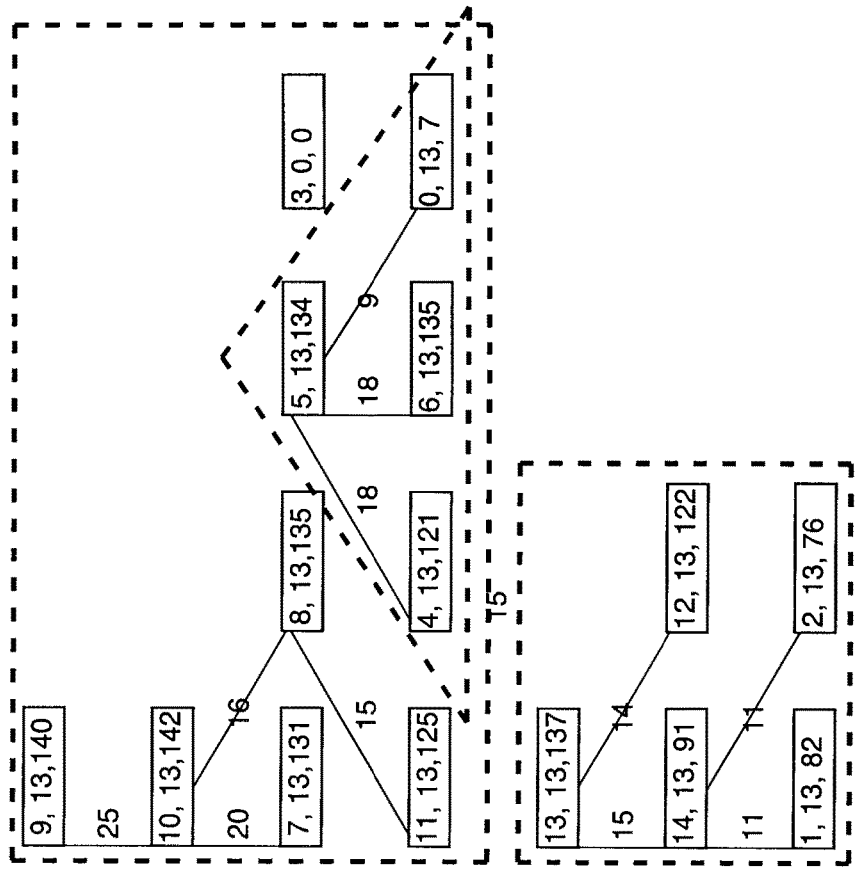
FIG. 11a discovers the optimal cluster configuration from the same AP cluster.

FIG. 11 shows a simple process for finding the optimal sub-cluster configuration. In one aspect, it first obtains a complete weighted graph using the distance between patterns as the edge weight. It then generates a maximum spanning tree from the complete. By cutting the edge one by one (beginning with the shortest distance). an increasing series of cluster configurations can be obtained. For the set of edges with the same weight, it cuts each of them in turn and obtains a different configuration for each cut and stores the separability measure for each configuration. FIG. 11 shows a "cluster configuration" that maximizes the average separability. Note that in this cluster configuration, the three clusters obtained correspond to mammals (in pink), plants (in green), insect (in yellow), and fungi (in blue). The bottom most cluster (subgraph) contain some patterns that pertain to all four classes (pattern 12 and pattern 2 in particular).

Relation-Graph of APs and AP Clusters

Another related invention is to discover and display the relationships (such as co-occurrence or relative position, or others) of Aligned Pattern Clusters (AP Cluster) on the same sequences (and later extended to functionally related sequences). Such relationships (co-occurrences or relative position, or others) may reveal the functional and long-distance dependence between AP Clusters. Here, a special Relational Graph known as Co-Occurrence Graph of APs and AP Clusters (denoted by AP Cluster C-Graph) is introduced. It is a weighted graph where the vertices are AP Clusters and the edges are the co-occurrence relationship between them with a co-occurrence measure as their weight.

The edges can represent other relations weighted by other measures, such as Jaccard Index or another measure reflecting relative position of APs and AP Clusters. Those will be other type of Relational Graph.

Figure 6:
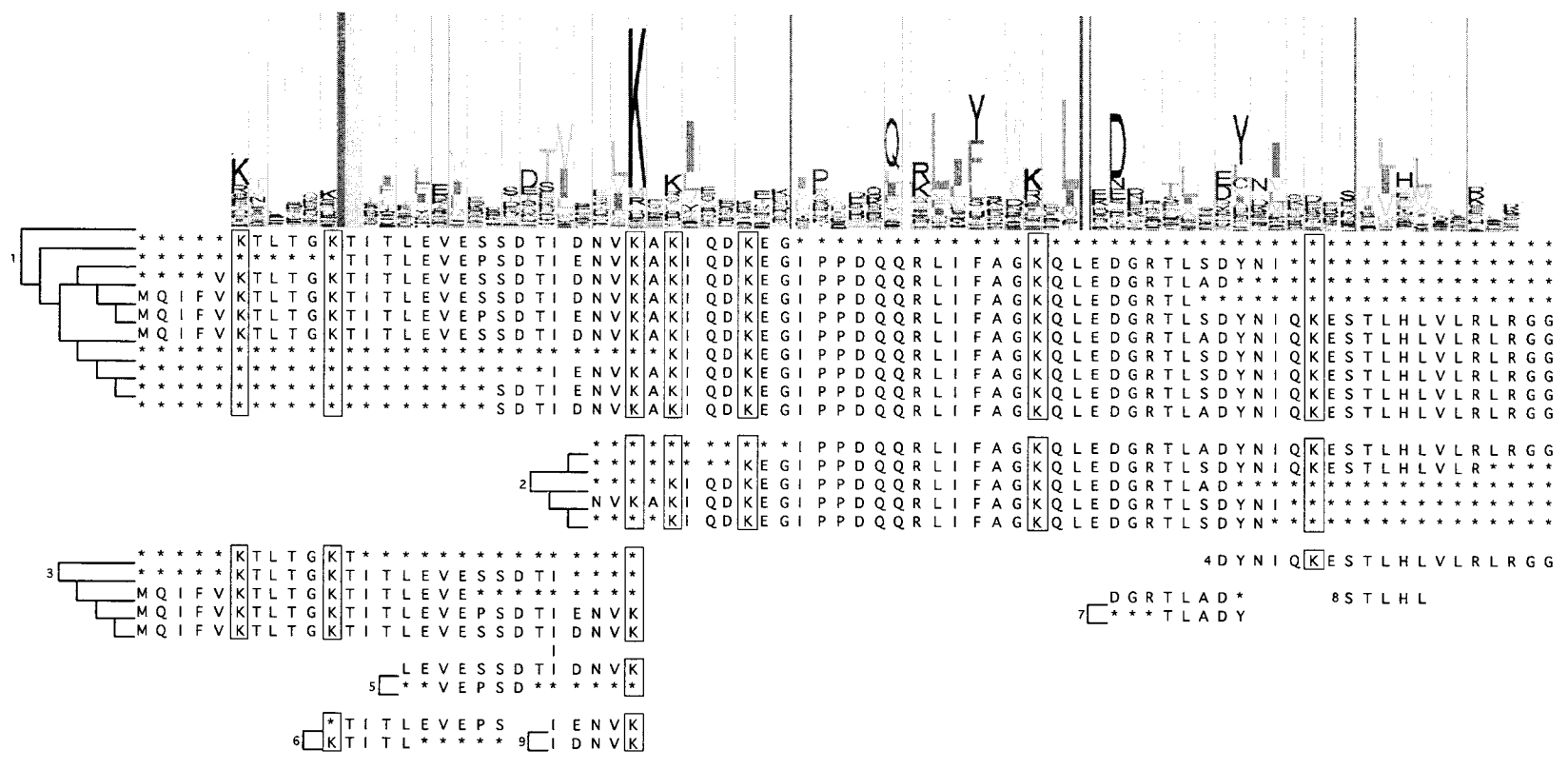
Figure 8:
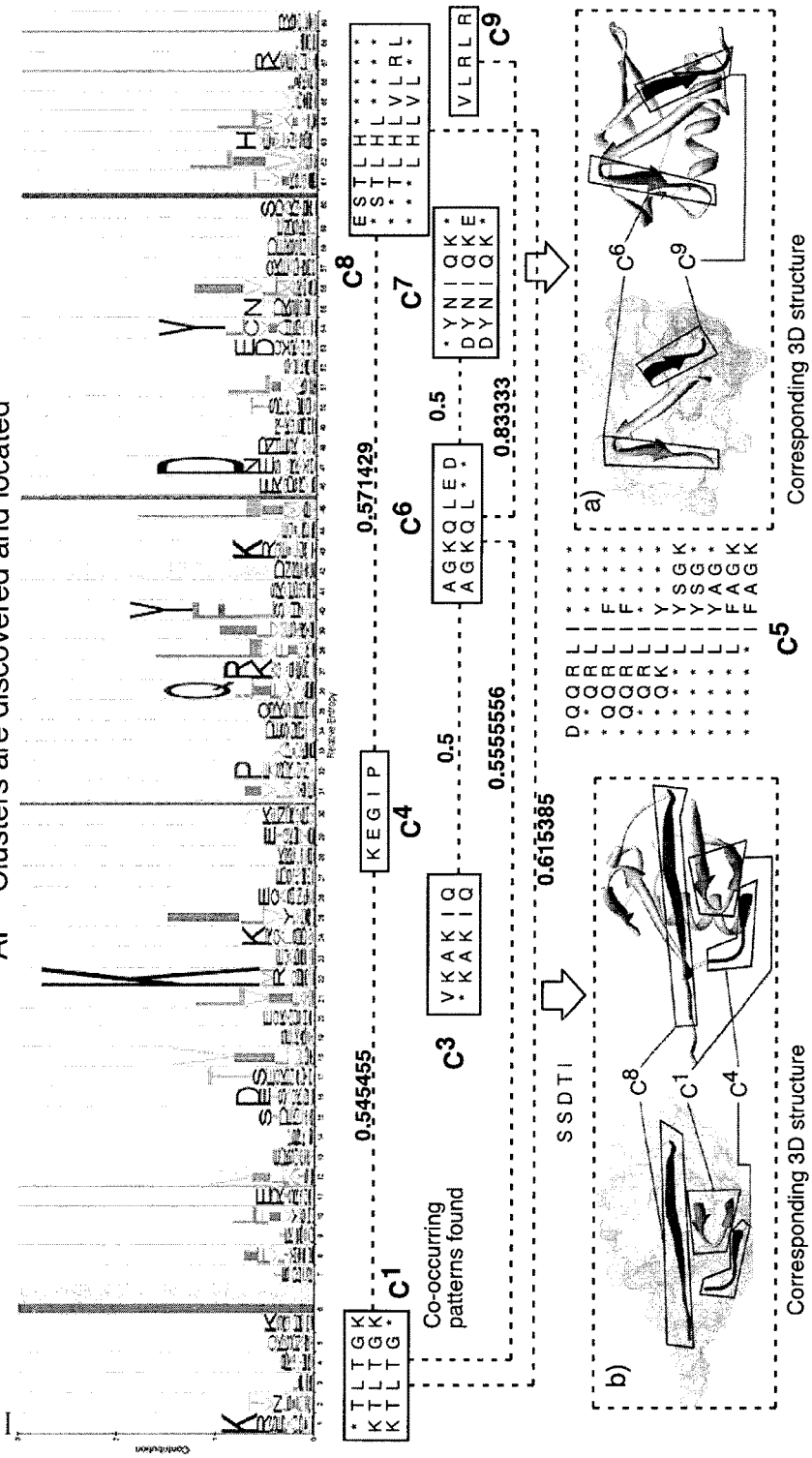
FIG. 8 shows further aspects of discovery and representation of co-occurring aligned pattern clusters of cytochrome c as well as integration of the results with 3D representations.

As an extension of the invention stated in the previous section, a AP Cluster C-Graph keeping the relative location of its AP Clusters (FIG. 8), or Exact Location when related back to the pFam multiple sequence alignment framework (HMM Logo) of the AP Clusters as shown in FIG. 6 is explained here. Another aspect of the invention, is the display of the AP Cluster C-Graph revealing the exact location of the AP Clusters in the family, as shown in FIG. 8.

Figure 9:
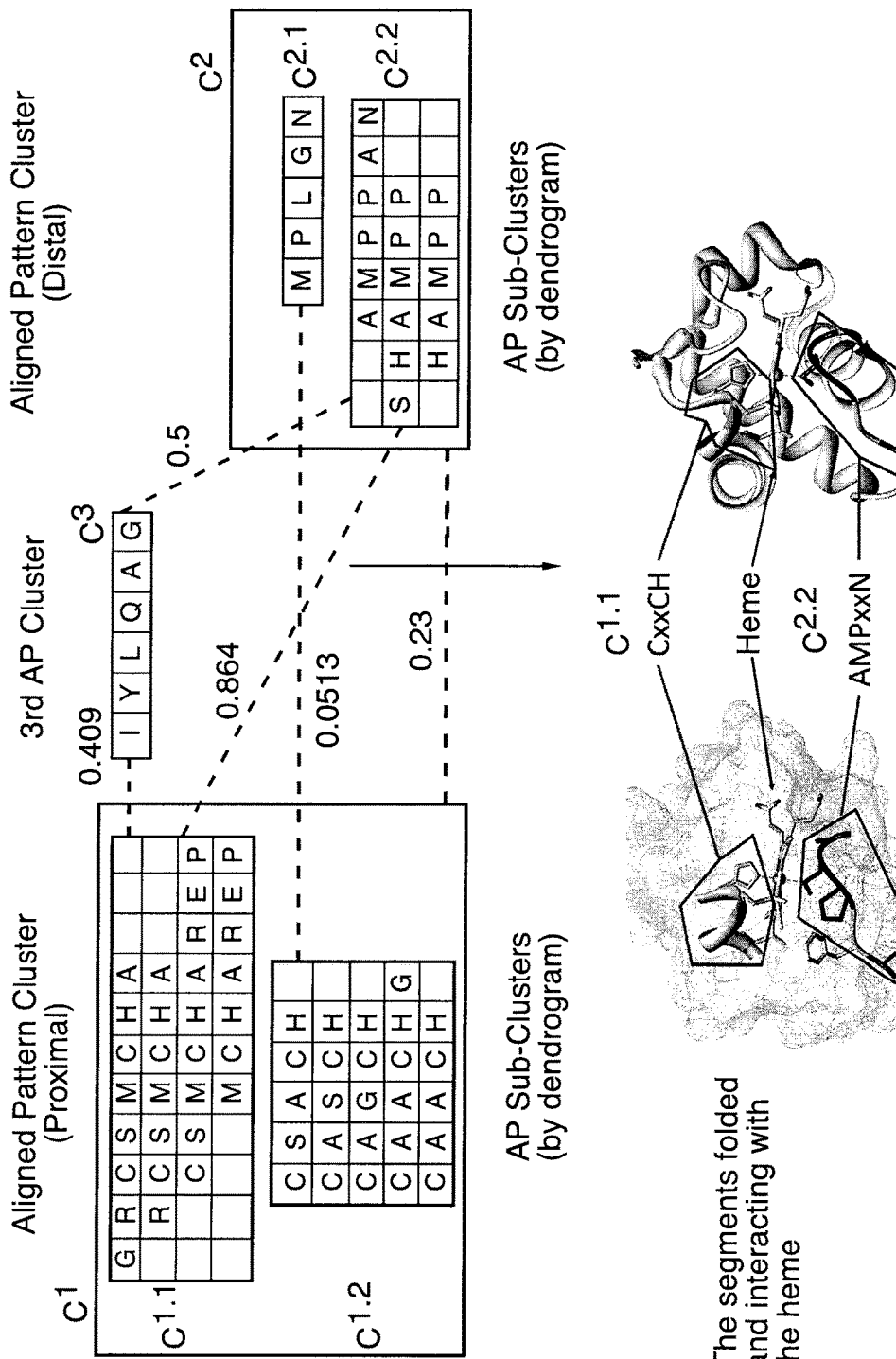
FIG. 9 illustrates co-occurring patterns and relational graph structure discovered using the invented method. The resulting complete sub-graphs correlate to AP Clusters and their corresponding 3 dimensional pictures of the protein.

The AP Cluster C-Graph can be displayed to reveal the level of co-occurrence if a threshold value of the co-occurrence measure is set. FIG. 8 is an example of the AP Cluster C-Graph for Uquibitin with a co-occurrence threshold set at 0.5 and FIG. 9 is an example of AP Cluster C-Graph for cytochrome c with a co-occurrence threshold set at 0.5.

Figure 11B:
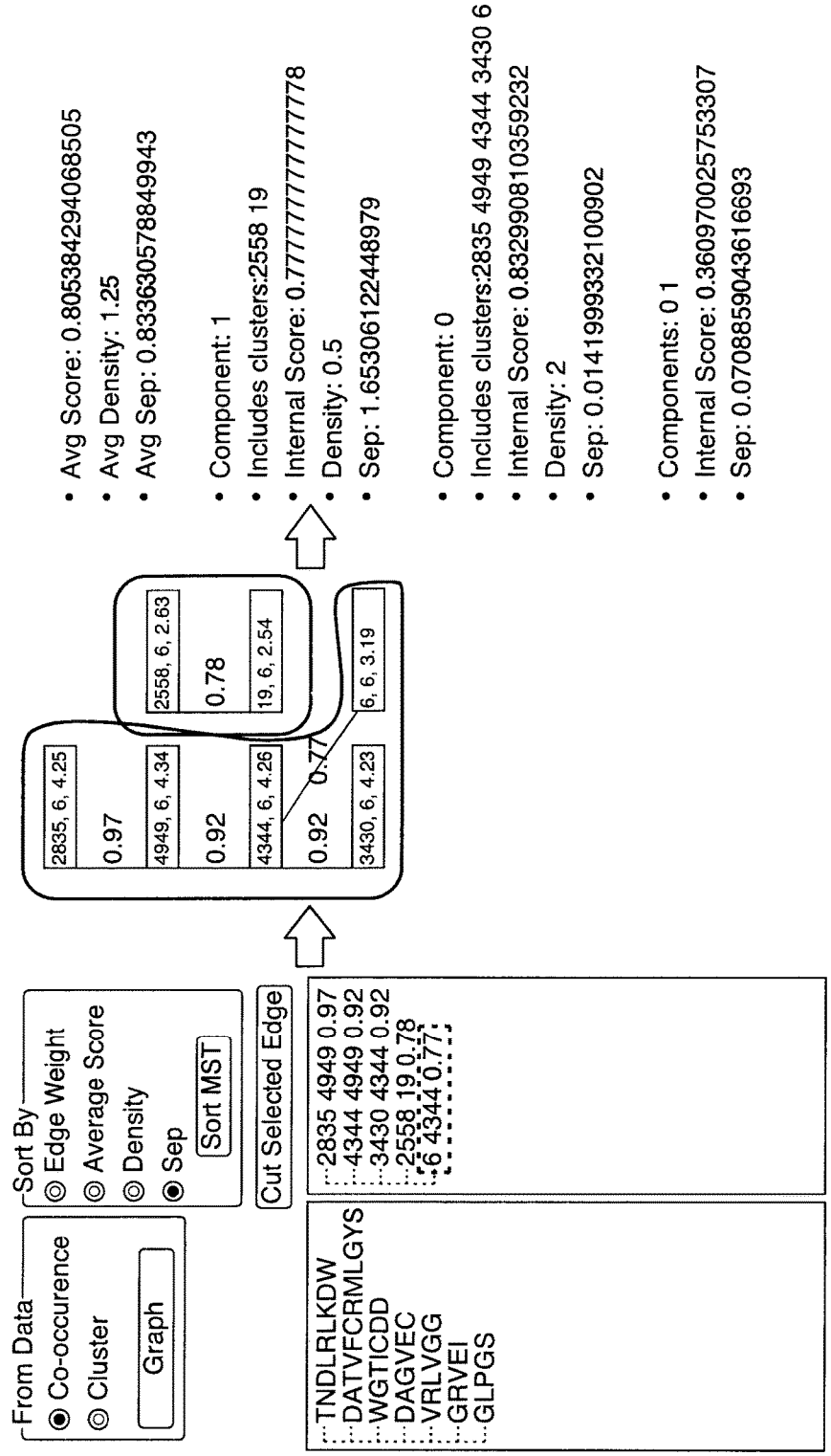
FIG. 11b further illustrates co-occurring patterns and relational graph structure discovered using the method. The AP Clusters are related to ensure higher co-occurrence relationships that are essential in the functional classification of the protein.

FIG. 11b shows the present version of the GUI for creating a AP Cluster C-Graph and partitioning the graph to maximize average separability. Note that in this cluster configuration, the two clusters obtained correspond to MARCO (in brown), SRA (in purple).

Co-Occurrence Measure

In support of creating the C-Graph to reveal potential protein interactions within a protein based solely on finding the co-occurring AP Clusters on protein sequences, a co-occurrence measure between AP Clusters is proposed. a sequence that share co-occurring patterns from two or more AP Clusters a pattern co-occurring sequences (PCS) is referred to. Co-occurring AP Cluster pairs can then be sorted by the number of PCS they share. An AP Cluster Co-Occurrence Measure is introduced which is defined as the proportion (i.e. the ratio) of the number of PCS over the number of the union of sequences covered by both AP Clusters to direct the sorting and also to serve as a threshold control the display of the C-Graph according to the degree of co-occurrence set by the co-occurrence measure.

APC pairs that contain most co-occurring patterns can be ranked and sorted. Hence, a score may be generated to direct the sorting of APCs pairs. Let C1 and C2 be two APCs discovered in the family. Then denote the number of pattern co-occurring sequences (PCS) shared by both APCs, or sequences that have patterns from both APCs, by |C1∩C2| and all the number of sequences in the union of C1 and C2 by |C1∪C2|. To select the dominating AP cluster or subcluster pairs, the pairs C1 and C2 can be sorted by ranking them based on the proportion of the number of |C1∩C2| over that of |C1∪C2|. This ratio may be the proportion measure which is denoted by $$Pr(C1, C2) = \frac{|C1 \cap C2|}{|C1 \cup C2|}$$

where

|C1∩C2|=the number of sequences with both patterns from APC C1 and APC C2

|C1∪C2|=the number of sequences with patterns from either APC C1 or APC C2

As $|C1 \cap C2|$ has to be positive and is less than or equal to $|C1 \cup C2|$, $Pr(C1, C2)$ is contained within $[1,0)$, and hence no additional normalization is needed. The normalized co-occurrence score $P\ r(C1, C2)$ (referred to also as co-occurrence) calculates the normalized proportion of the number of sequences that share common patterns over the entire union set associated with all the sequences in the APC pair. Thereafter, sorting based on $Pr(C1, C2)$, ensures that APCs with the higher sequence coverage, i.e. higher $|C1 \cup C2|$, are placed first. The two rankings can be created to be independent of each other rather than creating one single score incorporating both the sequence coverage and $P\ r(C1, C2)$, as we did not want the sequence coverage to ever undermine the $P\ r(C1, C2)$ ranking. For example, by ranking a APC pair with broad sequence coverage and low co-occurrence higher than a small APC pair with low sequence coverage and high co-occurrence could not be as meaningful since the latter APC pair is more valuable because its high co-occurrence would be less likely caused by noise. Moreover, having the co-occurrence taken the precedence may help to find intra-protein interactions that might be too small for other methods to notice.

The algorithm uses $P\ r(C1, C2)$ to calculate the co-occurrence not only because of its simplicity, but also because that it addresses all the related variables in this calculation, both explicitly and implicitly. Most importantly, putting the number of PCS sequences $|C1 \cap C2|$, as the numerator ensures a direct relationship between the increase in number of PCS and the score. To normalize the co-occurrence, the sequence union $|C1 \cup C2|$ is also used, which made the co-occurrence local to the APC pair. Thus, comparing APC pairs of different sizes became easier. Also, by having $|C1 \cup C2|$ as the normalizing factor, the differences, or the sequences having patterns from either APC but not both APCs, would be implicitly accounted for, since if the differences increased, that would be translated to an increase in the sequence union, and hence would cause a decrease in the score if the sequence co-occurrence did not increase also.

In another words, the AP Cluster pairs are ranked and sorted with the highest proportion measure down to the pair with the specified threshold set. To break ties, a secondary sorting a group of cluster pairs of the same ratio, the pair with the largest sequence coverage is first chosen.

Figure 17:
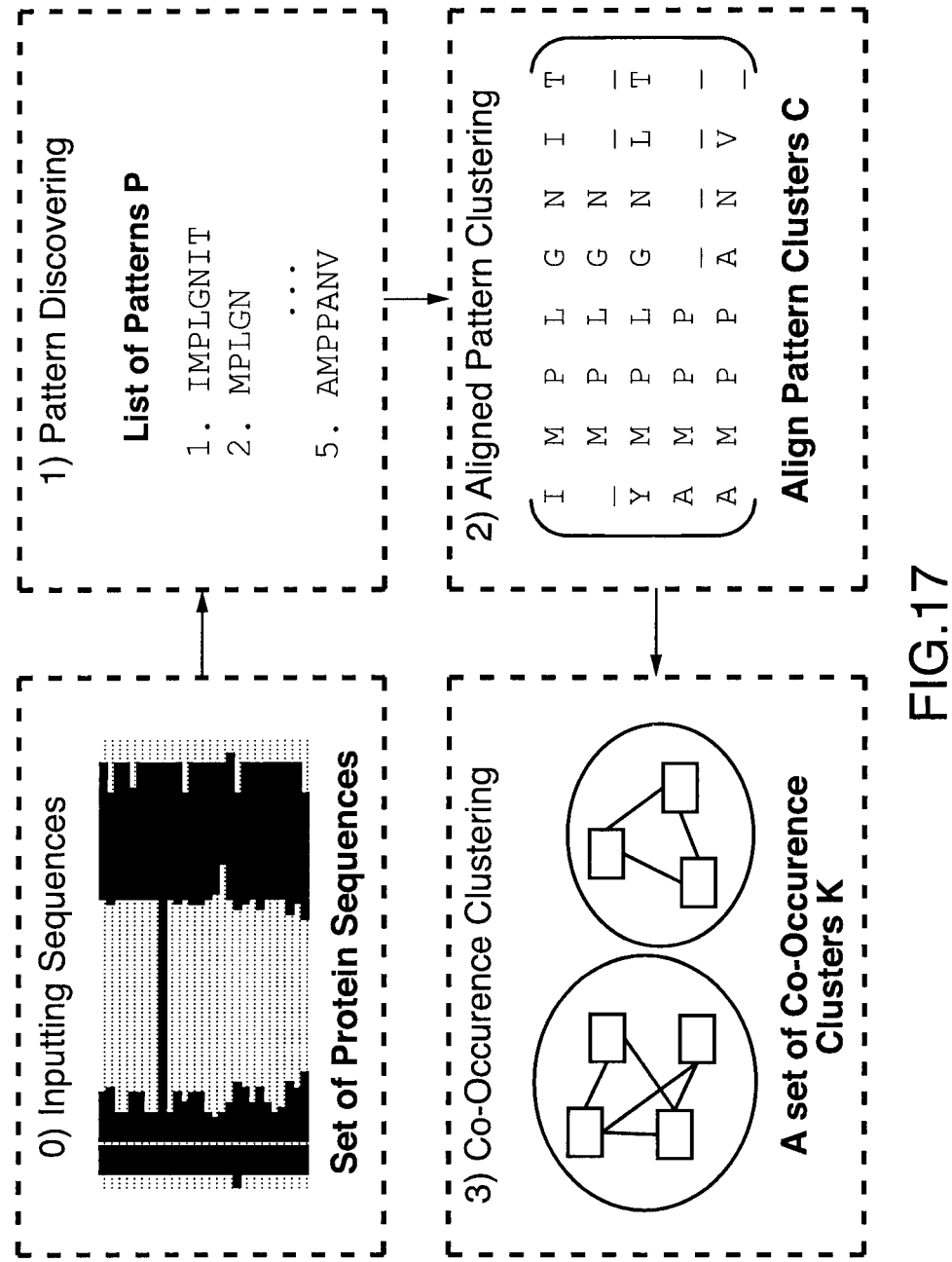
FIG. 17 illustrates an exemplary methodology combining three algorithms together to obtain the Co-occurrence Cluster of Aligned Pattern Clusters, in accordance with one aspect of the invention.

In one embodiment of the invention, an methodology combines three algorithms together to obtain the Co-occurrence Cluster of Aligned Pattern Clusters (Co-occurrence Cluster) (see e.g. FIG. 17). The first two algorithms are: 1) a pattern discovery algorithm described in this disclosure that discovers statistically significant sequence patterns from a set of sequences of a protein family while pruning the redundant patterns; 2) an Aligned Pattern Cluster (APC) described elsewhere in this disclosure, an algorithm that obtains compact aligned groups of statistically significant patterns referred to as APCs. These APCs contain variations with adjustable low information entropy. Finally, in the third algorithm, Co-occurrence Clusters are obtained by clustering the APCs discovered using spectral clustering with a co-occurrence score adopted as a measure of distance.

From the experiments run on ubiquitin, triosephosphate isomerase and cytochrome c, the proposed co-occurrence score is effective in finding the best candidate for intra-protein interactions. The candidates could be validated by their corresponding 3D structure of their respective protein family. The AP Cluster co-occurrence result reveals that the AP Clusters are all rather close in spatial distance, a notion that was not taken into account in the score calculations but inherent in the structure and function of the molecule.

Hence, there should be an physical/biological association between the high co-occurrence AP Clusters and their functional closeness of or interactions among their patterns even they are separated in spatial distance. Lastly, aside from the cytochrome c's results, due to a higher amino acid variation, all of the best AP Cluster candidates for intra-protein interaction came from the top AP Clusters (the most statistically significant functional units as conjectured). Even for cytochrome c, the best AP Cluster pair was only one level away from the top AP Clusters. These results shows that, working in complement with the clustering algorithm, the co-occurrence score can be used to find internal protein interaction in other protein families.

In the like manner and by the same measures, pattern co-occurrences could be extended across sequences if there are external evidences that those sequences of different types or families do bind together or interact with one another. Thus, the invention is able to be extended to study protein-protein, protein-RNA and RNA-RNA binding and interaction.

Classification

Once the AP cluster(s) and/or sub-cluster(s) is obtained based on the inherent residue associations and their similarity, the class labels are then incorporated to confirm that the discovered AP Clusters do reflect the biological ground truths about the protein family. a class measure is hereby introduced, called class information gain that reveals sequence patterns and their amino acid variations in association with the class labels incorporated into the AP Clusters after the AP Clustering process without relying on previous knowledge to assess how revealing are the AP Clusters in regards to the functionality in association with the taxonomical and/or other biological classes.

Shannon's Information Entropy for Class Labels.

To evaluate the class characteristics of an APC, each sequence from the set of input sequences in the experiment belongs to a particular class; thus, once a pattern is discovered, its original occurrences can be traced back to the input sequence for its class label. Therefore, in the supervised case, the distribution of the class labels associated with the pattern is used to calculate the class entropy, H, thereby measuring the association between the pattern and its class (es). If a pattern exists in only one class, its H will be 0, the best possible score. Conversely, if a pattern exists in classes fairly evenly, its H will be close to 1. Such association could be extended to H associating with other representations such as an APC, or an amino acid in a certain column of the APC. To expand the definition of class distribution from patterns to the other representations, the notion of class profile is introduced.

The class profile of a representation can be an n-tuple of ordered pairs that stores the name and the count of each class. Let $Y=\{y_1, y_2, \ldots, y_{[Y]}\}$, where $y_i=(name_i, count_i)$ such that name, is the class name, and count, is the class count for class $y_1$ among the $[Y]$ classes in the representation.

The class entropy for a representation can be computed from the distribution of the class profiles of that representation. It can be defined as follows:

$$H_y = -\sum_{i=1}^{[Y]} pr(y_i)(\text{Log}_{[Y]} pr(y_i)), \qquad (5)$$

where [Y] is the number of classes and $pr(y_1)$ is the probability of class i occurring in the input sequences restricted by that representation. The class entropy of the above representations are denoted as $H_Y(C^1)$ for an AP Cluster $C^1$; for a pattern $p^i$; $H_Y(c_j)$ for an aligned column $c_j$; and $H_Y(a(c_j))$ for a particular amino acid in the aligned columns $c_j$, $a(c_j)\in\Sigma(c_j)$.

The H for an APC can be obtained horizontally for a pattern, but it could also be obtained vertically for an aligned column. However, in an ARC, the vertical distribution of the class profile is the same for all aligned columns; therefore, the H for each aligned column is the same as that of the APC. Thus, the class information gain (IG) of an aligned column can measure the change in class information for each aligned column when the individual class profiles of the amino acids are taken into consideration.

To have a more objective way to study the amino acid variations with respect to the class labels provided from the taxonomical or other classification ground truth we introduce a new method with a new class discriminating measure, called class information gain, for ranking amino acid variations based on AP Clusters. Zero class information gain reveals no change in the distinct amino acids whereas aligned columns with high class information gain contain distinct amino acids associated with different classes. The effectiveness of these measures are revealed in the cytochrome c in FIG. 11.

The information gain can be expressed as:

$$\Delta H_y(c_j) = H_y(c_j) - \sum_{a(c_j)\in\Sigma(c_j)} (W_a(c_j)H_y(a(c_j))), \quad (7)$$

where $H_y(c_j)$ is the class entropy of the aligned column, $c_j$, note that $H_y(c_j)=H_y(C^1)$ and $H_y(a(c_j))$ is the amino acid class entropy. Let $W_a$ be the weight for normalizing the occurrences of the amino acid $a(c_j)$ or $\sigma(cj)$ in the aligned column $c_j$.

$$W_a(c_j) = \frac{countOcc(a(c_j))}{countOcc(c_j)} \quad (8)$$

which can also be thought of as the probability of $a(c_j)$ occurring in $c_j$.

Unsupervised Measures without Class Label

Information measure for each column in an APC that best is used to measure the aligned columns interdependencies in order to solve this problem. In an APC, the Entropy Redundancy (R1) is a measure that reflects the specificity and diversity of amino acids distributed in an aligned columns. Normalized Sum of Mutual Information Redundancy (SR2) is formulated as the normalized average of mutual information redundancy of an attribute. The R1 reflects amino acid variation in a column. The SR2 is the sum of all pairwise interdependence, computed as mutual information, between the current aligned column against that of all the other aligned columns in the APC. These measures are computed from the induced data of an APC.

Summary of Measures

There are various different measures used for ranking AP Clusters, AP Digraphs, and aligned columns.

| Machine Learning | Name | Space | Representation | Biological Equivalent |
|---|---|---|---|---|
| A1 Unsupervised | Coverage | $\mathbb{D}$ | AP Cluster | motif |
| A2 Unsupervised | Quality | $\mathbb{P}$ | AP Digraph | motif |
| A3 Unsupervised | Statistical Significance | $\mathbb{D}$ | AP Digraph | motif |
| B1 Unsupervised | R1 | $\mathbb{D}$ | aligned column | amino acid |
| B2 Unsupervised | R2 | $\mathbb{D}$ | aligned column | amino acid |
| C1 Semi-supervised | Class Entropy | $\mathbb{D}$ | AP Cluster | motifs |
| Semi-supervised | Class Entropy | $\mathbb{D}$ | pattern | motifs |
| Semi-supervised | Class Entropy | $\mathbb{D}$ | aligned column | amino acid |
| C2 Semi-supervised | Class Information Gain | $\mathbb{D}$ | aligned column | amino acid |

Overall Method and Computer System

Figure 3:
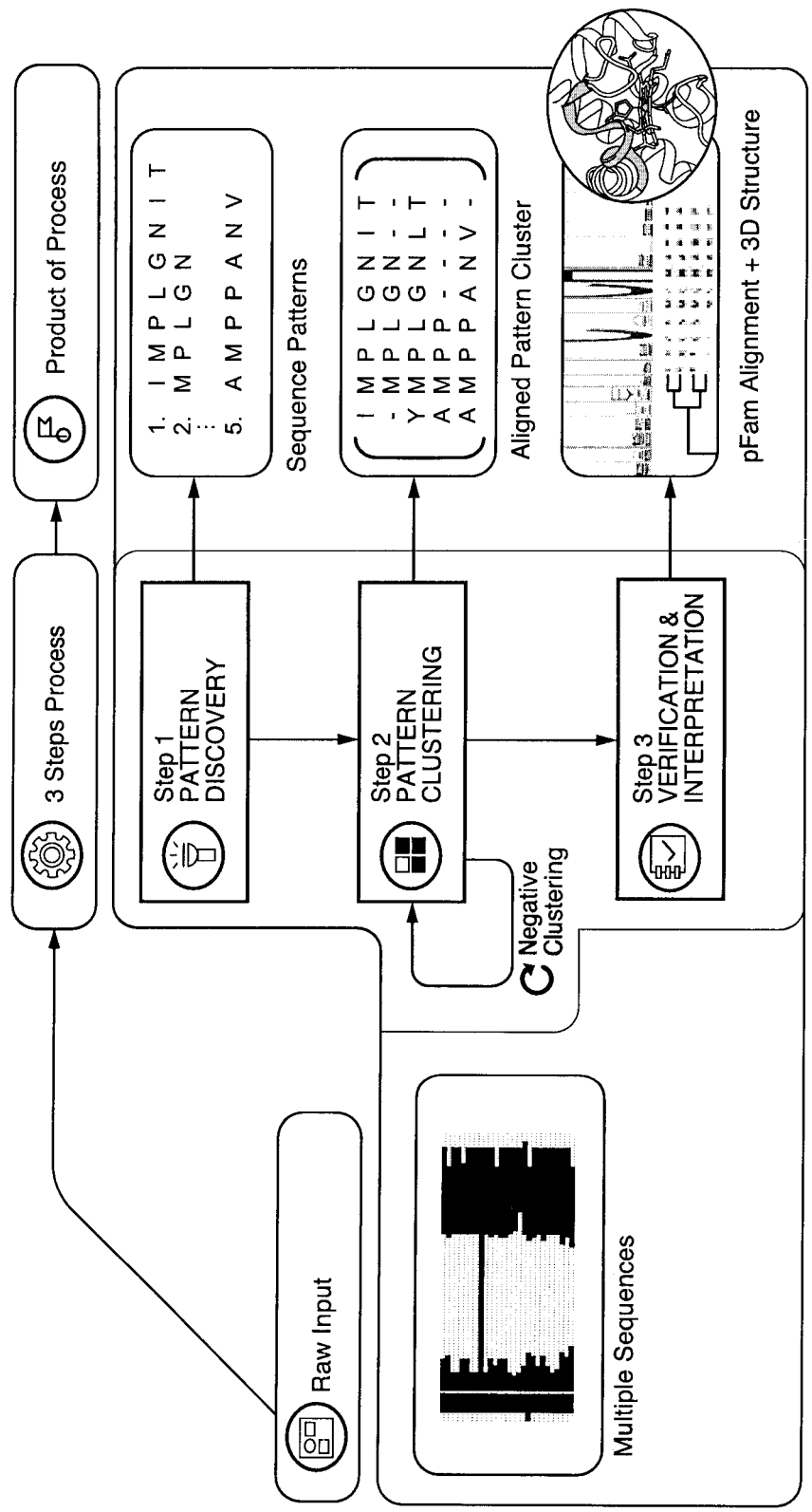
FIG. 3 is a workflow diagram that illustrates aspects of the method and computer system of the present invention.

FIG. 3 is a representative diagram illustrating both the steps of the method of the present invention, in one aspect thereof, as well as the resources of aspects of the computer system of the present invention. "Raw input" is obtained, and used for the 3-step process of the present invention, in one implementation of the present invention. In a first step, as explained earlier, one or more pattern discovery methods are used so as to generate sequence patterns. In a second step pattern clustering is applied, and may be applied iteratively, in order to generate aligned pattern clusters, and more specifically a ranked list of AP Clusters. In a third step, the ranked AP Clusters may be used in connection with one or more tools that enable one or more users to verify and/or interpret the results. For example, the results may be verified/interpreted using pFAM alignment and/or by applying the results of the method to one or more 3D visualization tools, as further explained below under the heading "Verification/Interpretation".

Figure 18:
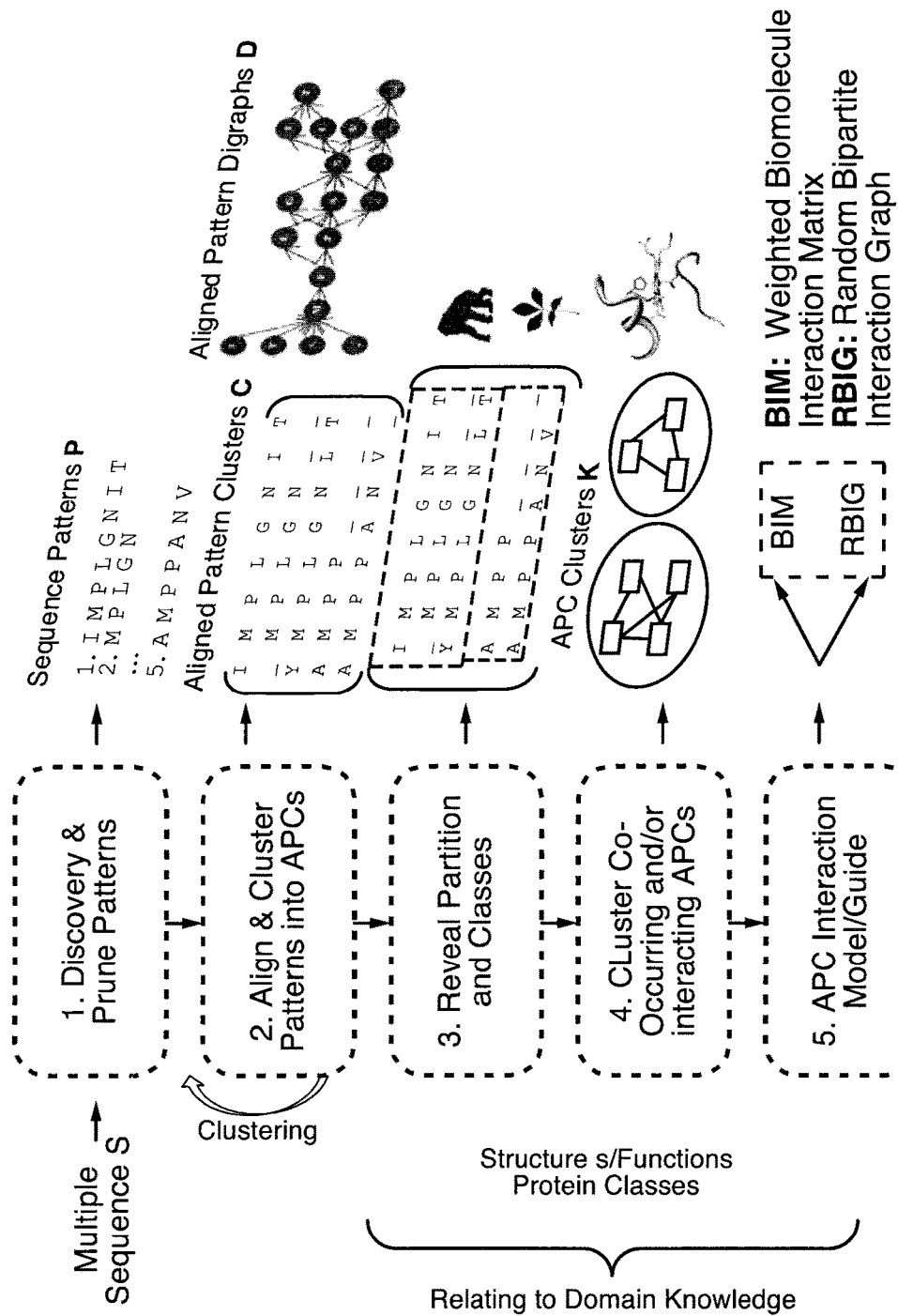
FIG. 18 demonstrates an exemplary process of discovering critical patterns and regions and relating them back to structures and functions to shorten the search time, in accordance with one aspect of the invention.

FIG. 18 demonstrates an exemplary process of discovering critical patterns and regions and relating them back to structures and functions to shorten the search time, in accordance with one aspect of the invention.

FIG. 19 further illustrates clusters of co-occurring APCs which suggest joint functionalities, in accordance with another aspect of the invention. In particular, as can be seen on FIG. 19, clusters of co-occurring APCs can suggest joint functionality.

A skilled reader will understand that the method of the present invention may be implemented for example using a suitable Clustering algorithm. Algorithm) below is only one example of such an algorithm.

---

Algorithm 1 The Single-Linkage Hierarchical Clustering Algorithm

Figure 7:
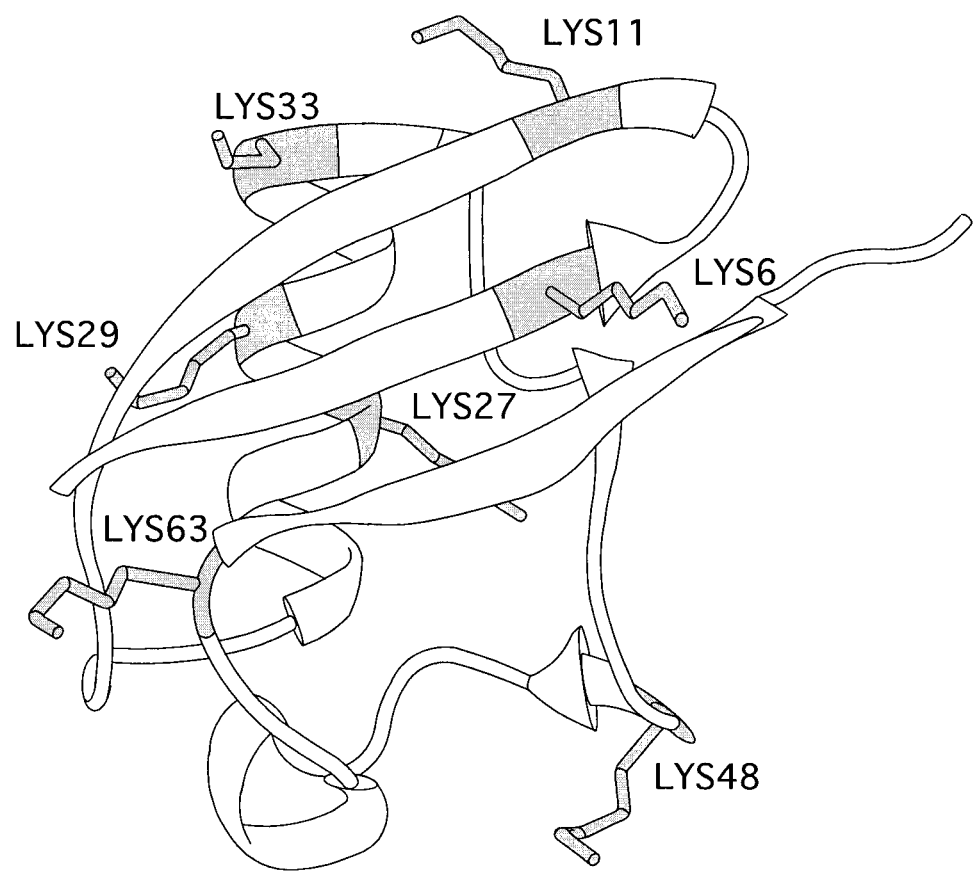
FIG. 7 is a further possible representation based on the present invention, in this case illustrating the use of the disclosed technology and a possible related representation for using discovery and location of AP clusters to show co-occurring aligned pattern clusters of ubiquitin, PDB id 1UBQ.

Require: $\mathbb{P} = \{P_1, ..., P_{|\mathbb{P}|}\}$, where $|\mathbb{P}| = m$
Ensure: $\mathbb{C} = \{C_1, ..., C_{|\mathbb{C}|}\}$
 1:   Set all $P_i \in \mathbb{P}$ as $C_i \in \mathbb{C}$
 2:   while (For all pairs of clusters $(C_i, C_j) \in \mathbb{C}$) do
 3:     Calculate SMILARITY($C_i$, $C_j$)
 4:   end while
 5:   while (! TERMINATION Conditions) do
 6:     Select max SIMILARITY($C_{maxi}$, $C_{maxj}$)
 7:     MERGE($C_{maxi}$, $C_{maxj}$) = $C_{new}$
 8:     Update list of clusters $\mathbb{C}$
 9:     while (For all pairs of clusters $(C_{new}, C_i)$) do
10:       Calculate SIMILARITY ($C_{new}$, $C_i$)
11:     end while
12:   end while Verification/Interpretation A possible implementation of the invention is illustrated by referring to the example of application of pattern discovery applied to the cytochrome c protein family, as shown in FIG. 4, FIG. 5, FIG. 9, FIG. 10, and FIG. 11, and to the ubiquitin protein family, as shown in FIGS. 6, 7, and 8.

Figure 4:
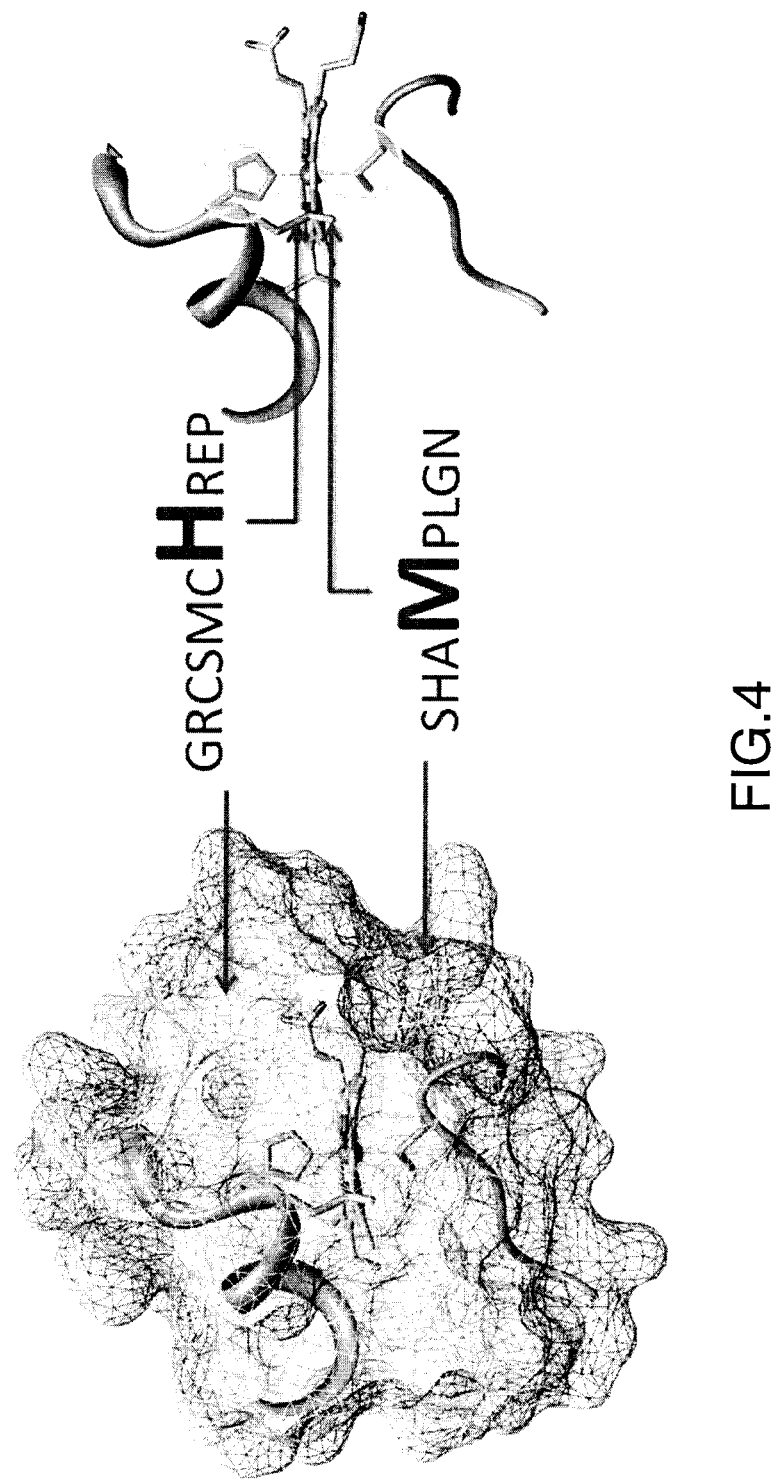
FIG. 4 illustrates a particular protein structure, namely 1F1F, and the data of association patterns to the 3D structure, generated based on the method of the present invention.

In one aspect of the invention, the computer system of the invention is linked or includes a mechanism for viewing the patterns discovered within the context of one or more 3D structures representing the macromolecular targets being discovered, for example the cytochrome c protein family as per images included in FIG. 4. A skilled reader will understand that many different representation or visualization methods are possible. What FIG. 4, and FIGS. 5, and 6 as well, illustrate that the present invention enables the use of unaligned raw data so as to render a comprehensive, unified graphical user interface ("GUI") for clustering and synthesizing AP Clusters so as to present comprehensive pattern quality results in a unified manner.

FIG. 4 right hand side in particular illustrates a representative 3D visualization of a particular structure, namely 1F1F. The two proposed synthesized patterns from the cytochrome c protein are the pink proximal binding segment and the blue distal binding segment. They are located in the heme binding site and they bind the heme ligand from above and below the horizontal plane, respectively. FIG. 4 left hand side specifically, one particular amino acid from each of the two protein segments binds the iron molecule located in the centre of the heme: the "H" (Histidine) residue at position 18 of the proximal segment and the "M" (Methionine) residue at position 62 of the distal segment.

Figure 5:
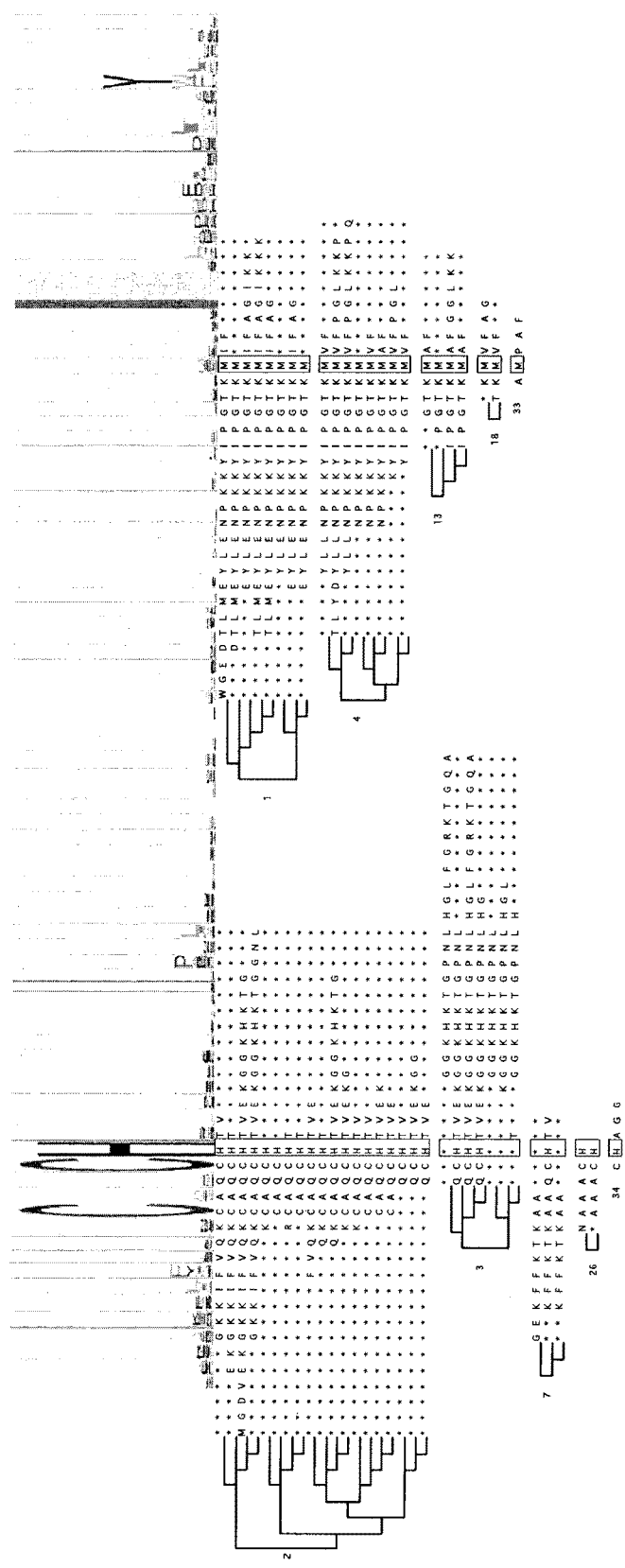

FIG. 5 illustrates one aspect of integration of pattern data generated by the present invention with aligned columns compared to pFAM results. FIG. 5 also shows a novel and innovative representation method wherein in this case ten resulting AP Clusters and its dendrogram representing the proximal and distal binding segments of the cytochrome c are compared to the HMM logo from pFam. In the largest AP Cluster, Cys17 is identified as one of the conserved aligned columns, where His18 binds to the home iron. In the second largest AP Cluster, Met62 is identified as one of the conserved aligned column of the distal binding segment, where Met62 binds the heme iron.

FIG. 6 illustrates an another example of the representation method using the ubiquitin protein family with three-dimensional structure of ubiquitin as shown in FIG. 7, and also shows the accuracy of the results generated by the present invention. In FIG. 6, seven Lys binding residues of the ubiquitin protein family are highlighted in the AP Cluster: Lys6, Lys11, Lys27, Lys29, Lys33, Lys48, and Lys63. Six of the seven binding sites are discovered, all except Lys29, are conserved aligned column with R1=1.0.

FIG. 7 illustrates another example of the 3D representation that incorporates pattern data generated using the present invention. In this case, a three-dimensional structure is depicted, namely the ubiquitin protein, with PDB ID 1UBQ from the protein data bank, showing seven binding residues: Lys6, Lys11, Lys27, Lys29, Lys33, Lys48, and Lys63.

One of the advantages of the present invention, as illustrated in FIGS. 4, 5, 6, 7, is that results of pattern discovery in accordance with the present invention can be represented in a unified manner so as to enable a user to discover relationships for verification or further analysis, whereas prior art solutions generally necessitate that such representation/analysis occur in several steps which may obscure such relationships.

FIG. 8 is a further possible representation based on the present invention, in this case illustrating use of the disclosed technology and a possible related representation for using discovery and location of AP clusters to show co-occurring aligned patterns and aligned pattern clusters obtained from the ubiquitin. Here, two sets of co-occurring aligned pattern clusters and their respective revealed 3D structure are shown.

FIG. 9 shows further aspects of discovery and representation of co-occurring aligned pattern clusters of ubiquitin as well as integration of the results with 3D representations in two visualization aspects.

Possible Implementation

A skilled reader will understand that the method of the present invention may be implemented as part of a computer system, and this computer system may be implemented in a number of different ways.

For example the computer system may consist of or link to a bioinformatics system, a drug discovery system, or research computer system that includes for example decision support features embodying the present invention. Another possible implementation of the present invention may consist of a personalized medicine system or medical record system that incorporates the pattern discovery features of the present invention, or functionality based on these features.

Figure 20:
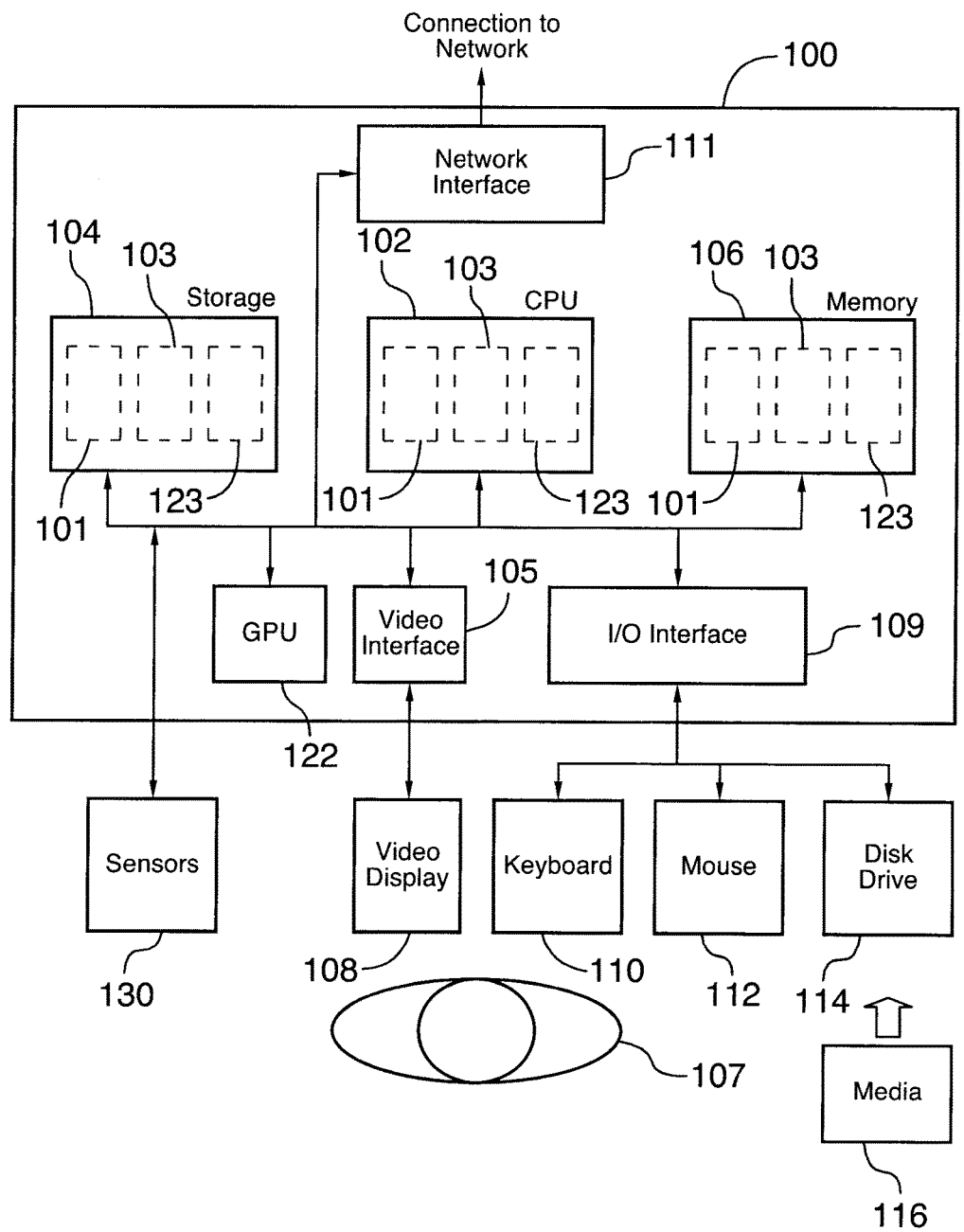
FIG. 20 illustrates a generic computer system for implementing the features and functions of the present invention.

In order to provide additional context for various aspects of the subject innovation, FIG. 20 and the following discussion are intended to provide a brief, general description of a suitable computing environment in which the various aspects of the present invention can be implemented.

A suitably configured computer device, and associated communications networks, devices, software and firmware may provide a platform for enabling one or more embodiments as described above. By way of example, FIG. 20 shows a generic computer device 100 that may include a central processing unit ("CPU") 102 connected to a storage unit 104 and to a random access memory 106. The CPU 102 may process an operating system 101, application program 103, and data 123. The operating system 101, application program 103, and data 123 may be stored in storage unit 104 and loaded into memory 106, as may be required. Computer device 100 may further include a graphics processing unit (GPU) 122 which is operatively connected to CPU 102 and to memory 106 to offload intensive image processing calculations from CPU 102 and run these calculations in parallel with CPU 102. An operator 107 may interact with the computer device 100 using a video display 108 connected by a video interface 105, and various input/output devices such as a keyboard 110, mouse 112, and disk drive or solid state drive 114 connected by an I/O interface 109. In known manner, the mouse 112 may be configured to control movement of a cursor in the video display 108, and to operate various graphical user interface (GUI) controls appearing in the video display 108 with a mouse button. The disk drive or solid state drive 114 may be configured to accept computer readable media 116. The computer device 100 may form part of a network via a network interface 111, allowing the computer device 300 to communicate with other suitably configured data processing systems (not shown). One or more different types of sensors may be used to receive input from various sources. The present system, method and apparatus may be practiced on virtually any manner of computer device including, for example, a desktop computer, laptop computer, tablet computer or wireless handheld.

It should be understood that further enhancements to the disclosed system, method and computer program are envisioned.

While the innovation has been described above in the general context of computer-executable instructions that may run on one or more computers, those skilled in the art will recognize that the innovation also can be implemented in combination with other program modules and/or as a combination of hardware and software.

Generally, program modules include routines/methods, programs, components, data structures, etc., that perform particular tasks or implement particular abstract data types. Moreover, those skilled in the art will appreciate that the inventive methods can be practiced with other computer system configurations, including single-processor or multi-processor computer systems, minicomputers, mainframe computers, as well as personal computers, handheld computing devices, microprocessor-based or programmable consumer electronics, and the like, each of which can be operatively coupled to one or more associated devices.

The illustrated aspects of the innovation may also be practiced in distributed computing environments where certain tasks are performed by remote processing devices that are linked through a communications network. In a distributed computing environment, program modules can be located in both local and remote memory storage devices. For example the knowledge database may be located remotely from a computer device that includes other elements of the correction utility, such that the correction utility queries the database for the cluster of related queries as described above, however the information distance operations described herein may below.

A computer (such as the computer(s) illustrated in the architecture described above) typically includes a variety of computer-readable media. Computer-readable media can be any available media that can be accessed by the computer and includes both volatile and non-volatile media, removable and non-removable media. By way of example, and not limitation, computer-readable media can comprise computer storage media and communication media. Computer storage media includes both volatile and non-volatile, removable and non-removable media implemented in any method or technology for storage of information such as computer-readable instructions, data structures, program modules or other data Computer storage media includes, but is not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or any other medium which can be used to store the desired information and which can be accessed by the computer. Communication media typically embodies computer-readable instructions, data structures, program modules or other data in a modulated data signal such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer-readable media.

What has been described above includes examples of the innovation. It is, of course, not possible to describe every conceivable combination of components or methodologies for purposes of describing the subject innovation, but one of ordinary skill in the art may recognize that many further combinations and permutations of the innovation are possible. Accordingly, the innovation is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

Cloud Computing

In one possible implementation, the pattern discovery features of the present invention may be implemented as part of a cloud computing resource or cloud-based computing resource. "Cloud computing" includes Internet based computing where shared resources, software and data are provided on demand. A "cloud" therefore can refer to a collection of resources (e.g., hardware, data and/or software) provided and maintained by an off-site party (e.g. third party), wherein the collection of resources can be accessed by an identified user over a network. The resources can include data storage services, word processing services, and many other general purpose computation (e.g., execution of arbitrary code) and information technological services that are conventionally associated with personal computers or local servers.

As used in this application, the terms "component" and "system" are intended to refer to a computer-related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution, and a component can be localized on one computer and/or distributed between two or more computers.

In general, the concepts of "virtual" and "cloud computing" include the utilization of a set of shared computing resources (e.g. servers) which are typically consolidated in one or more data center locations. For example, cloud computing systems may be implemented as a web service that enables a user to launch and manage computing resources (e.g., virtual server instances) in third party data centers. In a cloud environment, computer resources may be available in different sizes and configurations so that different resource types can be specified to meet specific needs of different users. For example, one user may desire to use small instance as a web server and another larger instance as a database server, or an even larger instance for processor intensive applications. Cloud computing offers this type of outsourced flexibility without having to manage the purchase and operation of additional hardware resources within an organization.

A cloud-based computing resource is thought to execute or reside somewhere on the "cloud", which may be an internal corporate network or the public Internet. From the perspective of an application developer or information technology administrator, cloud computing enables the development and deployment of applications that exhibit scalability (e.g., increase or decrease resource utilization as needed), performance (e.g., execute efficiently and fast), and reliability (e.g., never, or at least rarely, fail), all without any regard for the nature or location of the underlying infrastructure.

A number of factors have given rise to an increase in the utilization of cloud computing resources. For example, advances in networking technologies have significantly improved resource connectivity while decreasing connectivity costs. Advances in virtualization technologies have increased the efficiency of computing hardware by improving scalability and making it possible to more closely match computing hardware resources to the requirements of a particular computing task. Additionally, virtualization technologies commonly deployed in cloud computing environments have improved application reliability by enabling failover policies and procedures that reduce disruption due to an application or hardware failure.

It should be understood that the present invention may be extended by linking the invention with other technologies or processes useful in the monitoring, control or management of a variety of devices, for a variety of purposes.

In a further aspect of the invention, the computer system and computer implemented method of the present invention generates an Aligned Pattern (AP) Digraph, which simultaneously synthesizes similar motif patterns and identifies and tracks the variations in for example an amino acid (or RNA/DNA) composition. The vertices of the aligned pattern digraph identify amino acid (RNA/DNA) similarities and variations, which are then used to characterize or classify features. Significantly, this aspect of the present invention provides an unsupervised classification method that captures the most important amino acid (RNA/DNA) conservations and reveals the amino acid (RNA/DNA) variations that are important for semi-supervised classification.

Examples in Operation

As previously mentioned, the present invention was applied to the cytochrome c and ubiquitin protein families, AP Clusters were identified that correspond to the functional binding segments of both families and further that identified binding residues within the AP Cluster. The AP synthesis process of the present invention is faster than prior art combinatorial methods, and furthermore renders a more knowledge-rich representation, namely the AP Clusters and AP Digraphs, than the output from a prior art probabilistic method.

Advantages

Various advantages of the present invention have already been discussed. Further advantages are described as follows.

The present invention permits identification of protein/RNA/DNA family's function as well as intra and inter family interaction (protein-protein, protein-RNA, RNA-RNA) and also Protein/RNA/DNA characteristics, by finding applicable sequence patterns along with their variations, a computationally feasible way.

The present invention enables the use of amino acid variations to classify the protein ancestries based on its orthologous family classes and its functions based on its paralogous gene classes, whereas, the amino acid conservations to characterize the aligned pattern cluster subspace (or functional region).

The present invention also permits the use of RNA/DNA/Protein variation and co-occurrences of distant AP Clusters to reveal the structure and the function of RNA/DNA/Protein molecules.

The present invention avoids time-consuming simulations and experimentations that take enormous time and effort in biology experimentation and pattern analysis.

The present invention enables integration of statistical support into function discovery so as to enable more robust bioinformatics features.

The present invention permits unified visualization of associations across relatively unrelated sequences and substantially distal regions for the first time. This reduces research time and effort, and also permits discovery of unexpected associations that may be valuable.

The present invention enables more flexible research tools that provide more effective decision support to researchers, developers and healthcare organization.

The present invention improves the effectiveness of drug discovery and reduces costs. The present invention may be integrated with or link to with a variety of well established systems and methods used in research and development involving macromolecular information.

The present invention as broadly applicable to different domains of discovery and can be used to organize knowledge in ways that enable collaborative research. For example the technology described may be used to integrate genomic and proteomic data to support new and innovative discovery and visualization methods.

Other Features

It should be appreciated that the terminals, processors, or computers described herein may be embodied in any of a number of forms, such as a rack-mounted computer, a desktop computer, a laptop computer, or a tablet computer. Additionally, a computer may be embedded in a device perhaps not generally regarded as a computer but with suitable processing capabilities, including an electronic gaming machine, a Web TV, a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks. As used herein, the term "online" refers to such networked systems, including computers networked using, e.g., dedicated lines, telephone lines, cable or ISDN lines as well as wireless transmissions. Online systems include remote computers using, e.g., a local area network (LAN), a wide area network (WAN), the Internet, as well as various combinations of the foregoing. Suitable user devices may connect to a network for instance, any computing device that is capable of communicating over a network, such as a desktop, laptop or notebook computer, a mobile station or terminal, an entertainment appliance, a set-top box in communication with a display device, a wireless device such as a phone or smartphone, a game console, etc.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, embodiments may provide a tangible, non-transitory computer readable storage medium (or multiple computer readable storage media) (e.g., a computer memory, one or more floppy discs, compact discs (CD), optical discs, digital video disks (DVD), magnetic tapes, flash memories, circuit configurations in Field Programmable Gate Arrays or other semiconductor devices, or other non-transitory, tangible computer-readable storage media) encoded with one or more programs that, when executed on one or more computers or other processors, perform methods that implement the various embodiments discussed above. The computer readable medium or media can be transportable, such that the program or programs stored thereon can be loaded onto one or more different computers or other processors to implement various aspects as discussed above. As used herein, the term "non-transitory computer-readable storage medium" encompasses only a computer-readable medium that can be considered to be a manufacture (i.e., article of manufacture) or a machine and excludes transitory signals.

The terms "program" or "software" are used herein in a generic sense to refer to any type of computer code or set of computer-executable instructions that can be employed to program a computer or other processor to implement various aspects of as discussed above. Additionally, it should be appreciated that according to one aspect of this embodiment, one or more computer programs that when executed perform methods need not reside on a single computer or processor, but may be distributed in a modular fashion amongst a number of different computers or processors to implement various aspects of embodiments described herein.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags, addresses or other mechanisms that establish relationship between data elements.

Various aspects of embodiments described herein may be used alone, in combination, or in a variety of arrangements not specifically discussed in the embodiments described in the foregoing and the concepts described herein are therefore not limited in their application to the details and arrangement of components set forth in the foregoing description or illustrated in the drawings. For example, aspects described in one embodiment may be combined in any manner with aspects described in other embodiments.

Also, embodiments described herein may provide a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

While embodiments have been described with reference to certain exemplary features thereof, those skilled in the art may make various modifications to the described embodiments. The terms and descriptions used herein are set forth by way of illustration only and not meant as limitations. In particular, although embodiments have been described by way of examples, a variety of devices would practice the inventive concepts described herein. Embodiments have been described and disclosed in various terms, the scope of the embodiments is not intended to be, nor should it be deemed to be, limited thereby and such other modifications or embodiments as may be suggested by the teachings herein are particularly reserved, especially as they fall within the breadth and scope of the claims here appended. Those skilled in the art will recognize that these and other variations are possible as defined in the following claims and their equivalents.

The invention claimed is:

1. A computer-processor implemented method of determining sequence patterns with variations comprising:
   (a) accessing or acquiring a data set representing a family and several families of sequences of same and different kinds;
   (b) applying a pattern discovery technique or process to the sequences to generate, based on the data set representing the sequences, a series of patterns with statistically significant associations among their respective residues;
   (c) grouping and aligning the similar patterns into one or more Aligned Pattern Clusters that enable the analysis of multiple sequences that are in substantially distant regions and across families;
   (d) determining relations between Aligned Pattern Clusters to reveal distant and co-occurring functional and structural associations within the sequences, and extending these as between sequences which bind or interact with one another; and
   (e) using a class information gain variable to rank amino acid variations within the sequences, wherein one or more aligned columns within the Aligned Pattern Clusters contain distinct amino acids associated with different classes, wherein each class contains a distinct amino acid.

2. The method of claim 1, wherein the pattern discovery technique generates non-redundant, statistically significant associations between the sequences.

3. The method of claim 1, wherein the pattern discovery function determines a reduced list of non-redundant statistically significant association patterns, while the various residues of all patterns of the one or more Aligned Pattern Clusters are retained so as to capture or reveal the variations as well as the similarities therebetween.

4. The method of claim 1, comprising the further step of applying one or more statistical analysis methods to either generate additional variations or to support the analysis of the sequence patterns.

5. The method of claim 1, comprising the further step of using the Aligned Pattern Clusters to generate a knowledge-rich representation of the sequence patterns.

6. The method of claim 1, comprising the further step of introducing a separability measure thereby providing an autonomous method that is able to obtain separable and distinct sub-clusters from an Aligned Pattern Cluster without relying on prior knowledge or assumptions to reveal the inherent bio-information of sequence family and/or biological interactions.

7. The method of claim 1, wherein the sequences comprises a plurality of biosequences.

8. A system comprising one or more computers; the one or more computer comprising or being linked to a sequence pattern discovering utility, which when executed by a processor of the one or more computers:
   applies to a data set representing a family of sequences a pattern discovery function so as to generate a series of similar patterns with different lengths;
   groups and aligns the similar patterns into one or more Aligned Pattern Clusters that enable the analysis of multiple sequences that are not closely related or are in substantially distant regions, wherein the Aligned Pattern Clusters reveal distant and co-occurring functional and structural associations within the sequences; and
   uses a class information gain variable to rank amino acid variations within the sequences, wherein aligned columns within the Aligned Pattern Clusters contain distinct amino acids associated with different classes, wherein each class contains a distinct amino acid.

9. The system of claim 8, wherein one or more of the computers comprises or is linked to a display and the sequence pattern discovering utility includes or is linked to a visualization tool that uses the Aligned Pattern Clusters to generate a knowledge-rich representation of the sequence patterns.

10. The system of claim 8, wherein the sequence pattern discovering utility is further executed by the processor of the one or more computers to:
    determine relations between Aligned Pattern Clusters to reveal distant functional and structural associations within the sequences, and extending these as between sequences which bind or interact with one another.

11. The system of claim 10, wherein the sequence pattern discovering utility is further executed by the processor of the one or more computers to:
    determine co-occurring clustering relations between Aligned Pattern Clusters or within each Aligned Pattern Cluster.

12. The system of claim 11, wherein clusters of co-occurring relations suggest joint functionality.

13. The system of claim 8, wherein the sequences comprises a plurality of biosequences.

14. A system for determining sequence patterns with variations, the system comprising at least one server with a processor, the processor linked to a sequence pattern discovering utility, which when executed by the processor:
   (a) accesses or receives a data set representing a family and several families of sequences of same and different kinds;
   (b) applies a pattern discovery technique or process to the sequences to generate, based on the data set representing the sequences, a series of patterns with statistically significant associations among their respective residues;
   (c) groups and aligns the similar patterns into one or more Aligned Pattern Clusters that enable the analysis of multiple sequences that in substantially distant regions and across families;
   (d) determines relations between Aligned Pattern Clusters to reveal distant and co-occurring functional and structural associations within the sequences, and extending these as between sequences which bind or interact with one another; and
   (e) uses a class information gain variable to rank amino acid variations within the sequences, wherein aligned columns within the Aligned Pattern Clusters contain distinct amino acids associated with different classes, wherein each class contains a distinct amino acid.

15. The system of claim 14, wherein the pattern discovery technique generates non-redundant, statistically significant associations between the sequences.

16. The system of claim 14, wherein the pattern discovery function determines a reduced list of non-redundant statistically significant association patterns, while the various residues of all patterns of the one or more Aligned Pattern Clusters are retained so as to capture or reveal the variations as well as the similarities therebetween.

17. The system of claim 14, wherein the sequence pattern discovering utility is further operated to apply one or more statistical analysis methods to either generate additional variations or to support the analysis of the sequence patterns.

18. The system of claim 14, wherein the sequence pattern discovering utility is further operated to use the Aligned Pattern Clusters to generate a knowledge-rich representation of the sequence patterns.

19. The system of claim 14, wherein the sequence pattern discovering utility is further operated to introduce a separability measure thereby providing an autonomous method that is able to obtain separable and distinct sub-clusters from an Aligned Pattern Cluster without relying on prior knowledge or assumptions to reveal the inherent bio-information of sequence family and/or biological interactions.

20. The system of claim 14, wherein the sequences comprises a plurality of biosequences.

* * * * *

UNITED STATES PATENT AND TRADEMARK OFFICE
CERTIFICATE OF CORRECTION

PATENT NO. : 10,354,745 B2  Page 1 of 1
APPLICATION NO. : 14/784978
DATED : July 16, 2019
INVENTOR(S) : Andrew Ka-Ching Wong and Annie En-Shiun Lee It is certified that error appears in the above-identified patent and that said Letters Patent is hereby corrected as shown below:

On the Title Page

In Item (71) Applicant, "Andrew Ka-Ching Wong, Waterloo (CA)" should read as:
-- Andrew Ka-Ching Wong, Waterloo (CA); Annie En-Shiun Lee, Markham (CA)" --

Signed and Sealed this
Tenth Day of August, 2021

Drew Hirshfeld
*Performing the Functions and Duties of the*
*Under Secretary of Commerce for Intellectual Property and*
*Director of the United States Patent and Trademark Office*